(12) United States Patent
Kassem et al.

(10) Patent No.: US 9,636,070 B2
(45) Date of Patent: May 2, 2017

(54) METHODS, SYSTEMS, AND DEVICES FOR MONITORING AND DISPLAYING MEDICAL PARAMETERS FOR A PATIENT

(71) Applicant: DePuy Synthes Products, LLC, Raynham, MA (US)

(72) Inventors: Salim Kassem, North Attleboro, MA (US); Nicholas Baruch, North Smithfield, RI (US); Kenneth Creasy, Lakeville, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 534 days.

(21) Appl. No.: 13/803,667

(22) Filed: Mar. 14, 2013

(65) Prior Publication Data

US 2014/0275818 A1 Sep. 18, 2014

(51) Int. Cl.
*A61B 5/00* (2006.01)
*A61B 5/03* (2006.01)
*A61B 5/0205* (2006.01)

(52) U.S. Cl.
CPC ............. *A61B 5/742* (2013.01); *A61B 5/031* (2013.01); *A61B 5/7275* (2013.01); *A61B 5/746* (2013.01); *A61B 5/0205* (2013.01)

(58) Field of Classification Search
CPC ....... A61B 5/742; A61B 5/746; A61B 5/7435; A61B 5/7275
See application file for complete search history.

(56) References Cited

U.S. PATENT DOCUMENTS

| 2,396,351 A | 3/1946 | Thompson |
| 3,886,948 A | 6/1975 | Hakim |
| 3,960,142 A | 6/1976 | Elliott et al. |

(Continued)

FOREIGN PATENT DOCUMENTS

| AU | 729467 B2 | 2/2001 |
| DE | 42 11 045 A1 | 10/1993 |

(Continued)

OTHER PUBLICATIONS

U.S. Appl. No. 13/804,669, filed Mar. 14, 2013. (71 pages).

(Continued)

*Primary Examiner* — Tammie K Heller
(74) *Attorney, Agent, or Firm* — Mintz Levin Cohn Ferris Glovsky and Popeo, P.C.

(57) ABSTRACT

Methods, systems, and devices are provided for monitoring and displaying medical parameters for a patient. In one embodiment, a display screen can include information related to a physiological parameter being measured from a patient. The information can include a current value based on values of the physiological parameter gathered from the patient over a period of time. The display screen can indicate whether or not the current value is within a predetermined normal range for the physiological parameter and whether or not the current value is within a predetermined goal range for the physiological parameter. The goal range can be nested within the normal range. If the current value moves outside the normal range, an alarm can be triggered. A goal alarm can be triggered if the current value is within the normal range but falls outside the goal range.

22 Claims, 21 Drawing Sheets

(56) References Cited

U.S. PATENT DOCUMENTS

| | | |
|---|---|---|
| 3,976,278 A | 8/1976 | Dye et al. |
| 4,114,603 A | 9/1978 | Wilkinson |
| 4,135,509 A | 1/1979 | Shannon |
| 4,332,255 A | 6/1982 | Hakim et al. |
| 4,387,715 A | 6/1983 | Hakim et al. |
| 4,407,296 A | 10/1983 | Anderson |
| 4,421,124 A | 12/1983 | Marshall |
| 4,543,088 A | 9/1985 | Bootman et al. |
| 4,551,128 A | 11/1985 | Hakim et al. |
| 4,552,552 A | 11/1985 | Polaschegg et al. |
| 4,556,086 A | 12/1985 | Raines |
| 4,576,181 A | 3/1986 | Wallace et al. |
| 4,592,339 A | 6/1986 | Kuzmak et al. |
| 4,595,390 A | 6/1986 | Hakim et al. |
| 4,615,691 A | 10/1986 | Hakim et al. |
| 4,651,746 A | 3/1987 | Wall |
| 4,711,249 A | 12/1987 | Brooks |
| 4,727,887 A | 3/1988 | Haber |
| 4,772,257 A | 9/1988 | Hakim et al. |
| 4,781,680 A | 11/1988 | Redmond et al. |
| 4,785,822 A | 11/1988 | Wallace |
| 4,820,265 A | 4/1989 | DeSatnick et al. |
| 4,840,615 A | 6/1989 | Hancock et al. |
| 4,893,630 A | 1/1990 | Bray, Jr. |
| 4,937,037 A | 6/1990 | Griffiths et al. |
| 5,004,472 A | 4/1991 | Wallace |
| 5,009,662 A | 4/1991 | Wallace et al. |
| 5,021,046 A | 6/1991 | Wallace |
| 5,120,313 A | 6/1992 | Elftman |
| 5,121,470 A | 6/1992 | Trautman |
| 5,163,904 A | 11/1992 | Lampropoulos et al. |
| 5,201,753 A | 4/1993 | Lampropoulos et al. |
| 5,226,416 A | 7/1993 | Bethune et al. |
| 5,262,944 A | 11/1993 | Weisner et al. |
| 5,280,789 A | 1/1994 | Potts |
| 5,285,792 A | 2/1994 | Sjoquist et al. |
| 5,396,899 A | 3/1995 | Strittmatter |
| 5,425,713 A | 6/1995 | Taylor et al. |
| 5,431,629 A | 7/1995 | Lampropoulos et al. |
| 5,438,983 A | 8/1995 | Falcone |
| 5,449,345 A | 9/1995 | Taylor et al. |
| 5,464,012 A | 11/1995 | Falcone |
| 5,490,514 A | 2/1996 | Rosenberg |
| 5,522,387 A | 6/1996 | Simons |
| 5,549,654 A | 8/1996 | Powell |
| 5,591,171 A | 1/1997 | Brown |
| 5,622,869 A | 4/1997 | Lewis et al. |
| 5,701,906 A | 12/1997 | Alcidi et al. |
| 5,711,302 A | 1/1998 | Lampropoulos et al. |
| 5,716,342 A | 2/1998 | Dumbraveanu et al. |
| 5,721,382 A | 2/1998 | Kriesel et al. |
| 5,722,999 A | 3/1998 | Snell |
| 5,724,985 A | 3/1998 | Snell et al. |
| 5,785,043 A | 7/1998 | Cyrus et al. |
| 5,797,403 A | 8/1998 | DiLorenzo |
| 5,803,917 A | 9/1998 | Butterfield et al. |
| 5,891,046 A | 4/1999 | Cyrus et al. |
| 5,920,263 A | 7/1999 | Huttenhoff et al. |
| 5,928,182 A | 7/1999 | Kraus et al. |
| 5,935,083 A | 8/1999 | Williams |
| 5,938,669 A | 8/1999 | Klaiber et al. |
| 5,951,485 A | 9/1999 | Cyrus et al. |
| 5,970,801 A | 10/1999 | Ciobanu et al. |
| 5,991,664 A | 11/1999 | Seligman |
| 5,993,395 A | 11/1999 | Shulze |
| 5,993,398 A | 11/1999 | Alperin |
| 6,010,482 A | 1/2000 | Kriesel et al. |
| 6,067,991 A | 5/2000 | Forsell et al. |
| 6,071,267 A | 6/2000 | Zamierowski |
| 6,158,965 A | 12/2000 | Butterfield et al. |
| 6,171,252 B1 | 1/2001 | Roberts |
| 6,238,349 B1 | 5/2001 | Hickey |
| 6,241,661 B1 | 6/2001 | Schluess et al. |
| 6,262,728 B1 | 7/2001 | Alexander |
| 6,305,373 B1 | 10/2001 | Wallace et al. |
| 6,315,769 B1 | 11/2001 | Peer et al. |
| 6,322,502 B1 | 11/2001 | Schoenberg et al. |
| 6,416,291 B1 | 7/2002 | Butterfield et al. |
| 6,424,860 B1 | 7/2002 | Karlsson et al. |
| 6,432,040 B1 | 8/2002 | Meah |
| 6,470,213 B1 | 10/2002 | Alley |
| 6,481,292 B1 | 11/2002 | Reich |
| 6,485,462 B1 | 11/2002 | Kriesel |
| 6,503,208 B1 | 1/2003 | Skovlund et al. |
| 6,589,189 B2 | 7/2003 | Meyerson et al. |
| 6,779,851 B2 | 8/2004 | Bouchiere |
| 7,143,462 B2 | 12/2006 | Hohlbein |
| 7,616,991 B2 | 11/2009 | Mann et al. |
| 8,027,846 B2 | 9/2011 | Schoenberg et al. |
| 2001/0011543 A1 | 8/2001 | Forsell |
| 2002/0138512 A1 | 9/2002 | Buresh et al. |
| 2003/0023134 A1 | 1/2003 | Tracey |
| 2003/0093117 A1 | 5/2003 | Saadat |
| 2003/0144711 A1 | 7/2003 | Pless et al. |
| 2003/0172940 A1 | 9/2003 | Rogers et al. |
| 2003/0225371 A1 | 12/2003 | Hadzic et al. |
| 2004/0039256 A1 | 2/2004 | Kawatahara et al. |
| 2004/0054295 A1 | 3/2004 | Ramseth |
| 2004/0082904 A1 | 4/2004 | Houde et al. |
| 2004/0143212 A1 | 7/2004 | Trombley et al. |
| 2004/0193045 A1 | 9/2004 | Scarborough et al. |
| 2004/0215159 A1 | 10/2004 | Forsell |
| 2004/0215492 A1 | 10/2004 | Choi |
| 2004/0225203 A1 | 11/2004 | Jemison et al. |
| 2004/0249421 A1 | 12/2004 | Harel et al. |
| 2004/0260319 A1 | 12/2004 | Egle |
| 2004/0267377 A1 | 12/2004 | Egle |
| 2005/0038332 A1* | 2/2005 | Saidara ............... A61B 5/0002<br>600/347 |
| 2005/0065450 A1 | 3/2005 | Stuebe et al. |
| 2005/0070778 A1 | 3/2005 | Lackey et al. |
| 2005/0143668 A1 | 6/2005 | Lu et al. |
| 2005/0203360 A1 | 9/2005 | Brauker et al. |
| 2005/0240144 A1 | 10/2005 | Wassemann et al. |
| 2006/0064136 A1 | 3/2006 | Wang |
| 2006/0149161 A1 | 7/2006 | Wilson et al. |
| 2006/0189888 A1 | 8/2006 | Hassler et al. |
| 2006/0199997 A1 | 9/2006 | Hassler et al. |
| 2006/0200009 A1 | 9/2006 | Wekell et al. |
| 2006/0247722 A1 | 11/2006 | Maschino et al. |
| 2007/0156013 A1 | 7/2007 | Birk |
| 2007/0161919 A1* | 7/2007 | DiLorenzo ......... A61B 5/04001<br>600/544 |
| 2007/0161958 A1 | 7/2007 | Glenn |
| 2008/0096808 A1 | 4/2008 | Scaria |
| 2008/0172072 A1 | 7/2008 | Pool et al. |
| 2008/0221495 A1 | 9/2008 | Steffens et al. |
| 2008/0250341 A1 | 10/2008 | Dlugos et al. |
| 2009/0005703 A1 | 1/2009 | Fasciano |
| 2009/0113295 A1 | 4/2009 | Halpern et al. |
| 2009/0275807 A1 | 11/2009 | Sitzman et al. |
| 2010/0069725 A1 | 3/2010 | Al-Ali |
| 2010/0331651 A1 | 12/2010 | Groll |
| 2011/0193704 A1* | 8/2011 | Harper ............... A61B 5/14532<br>340/573.1 |
| 2011/0218406 A1 | 9/2011 | Hussain |
| 2011/0298621 A1 | 12/2011 | Shanbhag |
| 2014/0022256 A1 | 1/2014 | Carnes et al. |

FOREIGN PATENT DOCUMENTS

| | | |
|---|---|---|
| DE | 9416395 U1 | 12/1994 |
| EP | 0654232 A1 | 5/1995 |
| EP | 0 858 814 A1 | 8/1998 |
| EP | 0876808 A1 | 11/1998 |
| EP | 0941712 A1 | 9/1999 |
| EP | 1600120 A1 | 11/2005 |
| EP | 1649884 A1 | 4/2006 |
| EP | 1676527 A1 | 7/2006 |
| EP | 1 704 833 A2 | 9/2006 |
| EP | 1736123 A1 | 12/2006 |
| EP | 1815881 A1 | 8/2007 |
| EP | 1832252 A2 | 9/2007 |
| EP | 1832253 A1 | 9/2007 |

(56) References Cited

FOREIGN PATENT DOCUMENTS

| | | |
|---|---|---|
| EP | 1967168 A2 | 9/2008 |
| FR | 2730158 A1 | 8/1996 |
| GB | 1486822 A | 9/1977 |
| JP | 2004-513681 A | 5/2004 |
| JP | 2004-248793 A | 9/2004 |
| JP | 2004-261583 A | 9/2004 |
| JP | 2004-528123 A | 9/2004 |
| JP | 2004-344649 A | 12/2004 |
| JP | 2006175191 A | 7/2006 |
| RU | 2117459 C1 | 8/1998 |
| RU | 2002122333 A | 4/2004 |
| WO | 97/01370 A1 | 1/1997 |
| WO | 00/09047 A1 | 2/2000 |
| WO | 01/08597 A1 | 2/2001 |
| WO | 01/12078 A1 | 2/2001 |
| WO | 03/043534 A2 | 5/2003 |
| WO | 03/059422 A1 | 7/2003 |
| WO | WO-03091841 A2 | 11/2003 |
| WO | 03/105732 A1 | 12/2003 |
| WO | 2004/014245 A1 | 2/2004 |
| WO | 2006/018927 A1 | 2/2006 |
| WO | 2006/108203 A2 | 10/2006 |
| WO | 2006/118793 A2 | 11/2006 |
| WO | 2007/070906 A2 | 6/2007 |
| WO | 2008/088949 A1 | 7/2008 |
| WO | 2010/083498 A1 | 7/2010 |
| WO | WO-2014047171 A1 | 3/2014 |

OTHER PUBLICATIONS

[No Author Listed] "user's Manual HD2114.0-HD2134.0, HD2164.0-HD2114B.0, HD2114, 2-HD2134.2, HD2164.2-HD2114B; Rev. 1.0", Oct. 1, 2004, Delta Ohm, Via G. Marconi, 5-35020 Caselle Di Selvazzano(PD)—Italy, XP002376759, pp. 1-36.

[No Author Listed] Codman Brochure "ICP Express" © Codman & Shurtleff, Inc., 2001.

J.Ekstedt: "CSFS hydrodynamic studies in man, 1. Method of constant pressure CSF infusion", Journal of Neurology, Neurosurgery and Psychiatry; vol. 40, 1977, pp. 105-119.

Shapiro, K. et al.: "Characterization of Clinical CSF Dynamics and Neural Axis Compliance Using the Pressure-Volume Index: I. the Normal Presure-Volume Index", Annals of Neurology, vol. 7, No. 6, Jun. 1980; pp. 508-514.

Suga et al., "Instantaneous Pressure-Volume Relationships and Their Ratio in the Excised, Supported Canine Left Ventricle," Circ. Res. 1974, 35, 117-126.

Greenway et al., "Comparison of the Effects of the Heptatic Nerve Stimulation on Arterial Flow, Distriubtion of Arterial Portal Flows and Blood Content in the Livers of Anaesthetized Cats and Dogs," J. Physiol. 1972, 227, 487-501.

Extended search report issued in European Application No. 14159616.3 dated Jun. 18, 2014.

\* cited by examiner

METHODS, SYSTEMS, AND DEVICES FOR MONITORING AND DISPLAYING MEDICAL PARAMETERS FOR A PATIENT

FIELD

The present disclosure relates generally to methods, systems, and devices for monitoring and displaying medical parameters for a patient.

BACKGROUND

Patient monitoring can take a variety of forms and can gather a wide variety of physiological data. The display of such data, including what is displayed and how it is displayed, can affect the ability of caregivers, such as doctors and nurses, to interpret and act on the data. For example, intracranial pressure (ICP) is a standard monitoring modality for traumatic brain injury patients. Medical guidelines may prescribe threshold values for intracranial pressure. The guidelines of the Brain Trauma Foundation, for example, indicate that clinical action should be taken to reduce intracranial pressure if the intracranial pressure exceeds 20-25 mmHg. However, numerous factors can cause transient changes to intracranial pressure, including patient physiology, monitoring system noise, and actions taken by a caregiver.

To monitor a patient, caregivers typically use monitoring devices such as the Codman ICP Express device 100, which is shown in FIG. 1, available from Codman & Shurtleff, Inc. of Raynham, Mass. As shown, the device 100 has a display of intracranial pressure and a display of systolic and diastolic values for the intracranial pressure, as well as an alarm. A caregiver can look at the display to ascertain the intracranial pressure. Caregivers also use charts, e.g., a caregiver can manually record an event in a chart associated with a patient.

One drawback with current monitoring devices is that the devices only provide a limited amount of patient data. Caregivers thus only have a limited picture of a patient's condition from a monitoring device on which to base decision making regarding treatment of the patient. It can therefore be difficult for caregivers to make clinical decisions based on the patient data displayed on a monitoring device without taking additional time to review other patient records, e.g., paper files. Taking this additional time can adversely affect patient treatment, particularly in critical care situations, such as situations involving traumatic brain injury patients, where treatment delays can greatly exacerbate injuries or otherwise be particularly problematic. Moreover, such considerations are applicable not just to intracranial pressure, but to a wide variety of patient monitoring modalities involving other physiological parameters.

Accordingly, there remains a need for improved methods, systems, and devices for monitoring and displaying medical parameters for a patient.

SUMMARY

Methods, systems, and devices are provided for monitoring and displaying medical parameters for a patient. In one embodiment, a system is provided that includes a display screen and a processor. The processor is configured to receive a plurality of values of a physiological parameter measured from a patient over a period of time, determine if a current value based on the received values is within a normal range of the physiological parameter, cause an alarm indicator to be displayed on the display screen if the current value is determined to not be within the normal range, determine if the current value is within a goal range of the physiological parameter, and cause a goal indicator to be displayed on the display screen if the current value is determined to be within the goal range. The goal range is nested within the normal range. The alarm indicator is not displayed on the display screen if the current value is determined to be within the normal range. The goal indicator is not displayed on the display screen if the current value is determined to not be within the goal range. The physiological parameter can be at least one of intracranial pressure (ICP), cerebral perfusion pressure (CPP), mean arterial blood pressure (MAP), oxygen saturation ($pO_2$), heart rate, and temperature.

In another aspect, a method is provided. In one embodiment, the method includes receiving a plurality of values of a physiological parameter measured from a patient over a period of time, determining if a current value based on the received values is within a normal range of the physiological parameter, causing an alarm indicator to be displayed on the display screen if the current value is determined to not be within the normal range, determining if the current value is within a goal range of the physiological parameter, and causing a goal indicator to be displayed on the display screen if the current value is determined to be within the goal. The goal range is nested within the normal range. The alarm indicator is not displayed on the display screen if the current value is determined to be within the normal range. The goal indicator is not displayed on the display screen if the current value is determined to not be within the goal range.

The method can vary in any number of ways. For example, causing the goal indicator to be displayed on the display screen can include changing a color shown in a first portion of the display screen, and causing the alarm indicator to be displayed on the display screen comprises changing a color shown in a second portion of the display screen. For another example, the physiological parameter can be at least one of ICP, CPP, MAP, $pO_2$, heart rate, and temperature.

The method can include determining if a plurality of the values match a predetermined pattern. The goal indicator can not be displayed on the display screen if the plurality of values are determined to match the predetermined pattern even if the current value is determined to be within the goal range. The predetermined pattern can include at least one of the plurality of values continuously increasing toward an upper limit of the normal range and the plurality of values continuously decreasing toward a lower limit of the normal range. A number of the plurality of values can be a predetermined number.

The display screen can be attached to a housing. In some embodiments, the determining if the current value is within the normal range, the causing the alarm indicator to be displayed, the determining if the current value is within the goal range, and the causing the goal indicator to be displayed can be performed by a processor disposed in the housing. In some embodiments, the determining if the current value is within the normal range, the causing the alarm indicator to be displayed, the determining if the current value is within the goal range, and the causing the goal indicator to be displayed can be performed by a processor remotely located from the housing.

A computer readable medium can be provided that has stored thereon a program, that when executed, can perform the method.

In another embodiment, a method includes receiving data representing a value of a physiological parameter over a time period. The physiological parameter is measured from a patient. The method also includes displaying, on a monitoring screen, a current value based on the received values, and determining if the current value is within a goal range of the physiological parameter. The goal range has a predetermined upper limit and a predetermined lower limit. If the current value is determined to be within the goal range, a visual goal indicator indicating that the current value is within the goal range is caused to be displayed on the monitoring screen. The goal indicator is not displayed on the monitoring screen if the current value is determined to not be within the goal range. The method can also include determining if the current value is within a normal range of the physiological parameter. The normal range has a predetermined upper limit that is greater than the predetermined upper limit of the goal range and has a predetermined lower limit that is less than the predetermined lower limit of the goal range. If the current value is determined to be outside the normal range, a visual alarm indicator indicating that the current value is outside the normal range is caused to be displayed on the monitoring screen. The alarm indicator is not displayed on the monitoring screen if the current value is determined to be within the normal range. In some embodiments, the physiological parameter can be at least one of ICP, CPP, MAP, $pO_2$, heart rate, and temperature.

The method can have any number of variations. For example, causing the visual goal indicator to be displayed on the monitoring screen can include changing a color shown in a first portion of the monitoring screen adjacent the current value, and causing the visual alarm indicator to be displayed on the monitoring screen can include changing a color shown in a second portion of the monitoring screen adjacent the current value. For another example, the goal indicator can not be displayed on the monitoring screen if the alarm indicator is displayed on the monitoring screen, and the alarm indicator can not be displayed on the monitoring screen if the goal indicator is displayed on the monitoring screen. For yet another example, the method can include continuously repeating the determining if the current value is within the goal range so as to continuously update on the monitoring screen whether or not the goal indicator is displayed on the monitoring screen, and continuously repeating the determining if the current value is within the normal range so as to continuously update on the monitoring screen whether or not the alarm indicator is displayed on the monitoring screen. For another example, the method can include receiving data representing a value of a second physiological parameter over the time period and changing at least one of the predetermined upper limit of the goal range and the predetermined lower limit of the goal range based on an current value of the value of the second physiological parameter over the time period. The second physiological parameter can be measured from the patient. For another example, the method can include setting the predetermined upper limit of the goal range and the predetermined lower limit of the goal range in response to a manual user input indicating the predetermined upper limit of the goal range and the predetermined lower limit of the goal range. For yet another example, the method can include pre-programming the predetermined upper limit of the goal range and the predetermined lower limit of the goal range based on a typical normal range of the physiological parameter.

In some embodiments, the method can include receiving data representing a value of one or more additional physiological parameters over time. Each of the one or more additional physiological parameters can be measured from the patient. The method can also include displaying, on the monitoring screen, a graphical representation of an current value of each of the one or more additional physiological parameters over the time period, and determining if the current value of each of the one or more additional physiological parameters is within a respective goal range for each of the one or more additional physiological parameters. Each of the respective goal ranges can have a predetermined upper limit and a predetermined lower limit. If the current value of any of the one or more additional physiological parameters is determined to be within its associated goal range, a visual goal indicator indicating that the current value is within the goal range can be caused to be displayed on the monitoring screen. The goal indicator for the one or more additional physiological parameters can not be displayed on the monitoring screen if its associated current value is determined to be outside its associated goal range. The method can also include determining if the current value of each of the one or more additional physiological parameters is within a respective normal range for each of the one or more additional physiological parameters. Each of the respective normal ranges can have a predetermined upper limit that is greater than the predetermined upper limit of its associated goal range and can have a predetermined lower limit that is less than the predetermined lower limit of its goal range. If the current value of any of the one or more additional physiological parameters is determined to be outside its associated normal range, a visual alarm indicator indicating that the current value is outside the normal range can be caused to be displayed on the monitoring screen. The alarm indicator for the one or more additional physiological parameters can not be displayed on the monitoring screen if its associated current value is determined to be within its associated normal range.

BRIEF DESCRIPTION OF DRAWINGS

This invention will be more fully understood from the following detailed description taken in conjunction with the accompanying drawings, in which.

DETAILED DESCRIPTION

Figure 1:
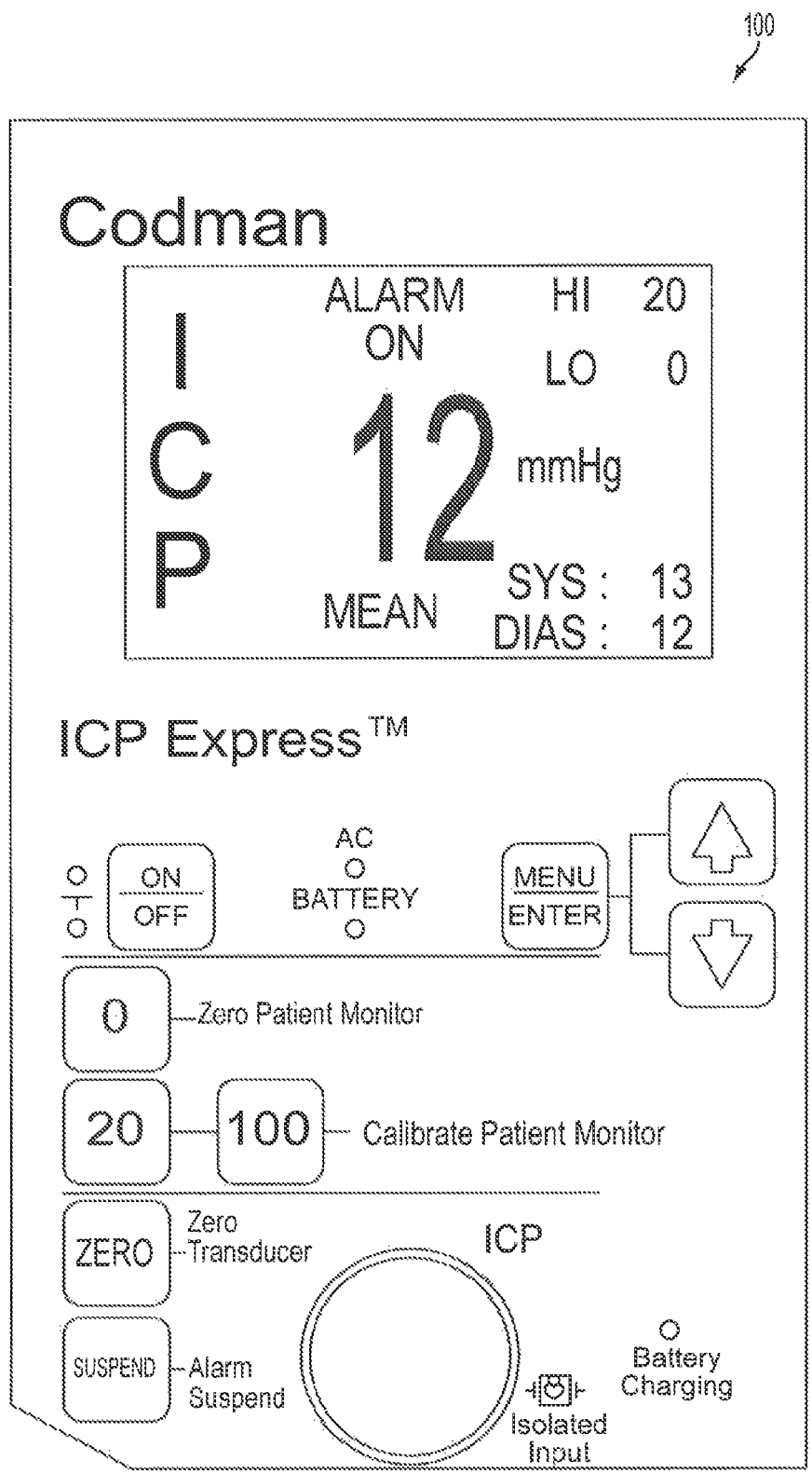
FIG. 1 (PRIOR ART) is a schematic diagram of a monitoring device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Methods, systems, and devices are provided for monitoring and displaying medical parameters for a patient. In general, the methods, systems, and devices can facilitate monitoring of a patient, such as when the patient is being treated at a hospital or other medical facility at which the patient's condition can require regular observation. The methods, systems, and devices can allow the displaying and monitoring of one or more physiological parameters of the patient. This monitoring and display can facilitate identification of changes in the patient's condition that may require a doctor's assessment and/or may require an adjustment of the patient's treatment, e.g., administration of medication(s), administration of oxygen, adjustment of one or more settings of an implanted medical device, adjustment of an elevated limb's position, additional hydration, movement to another hospital unit, etc. Generally, as will be appreciated by a person skilled in the art, the earlier the change in the patient's condition can be detected, the more time medical personnel can have to assess and effectively address the change. The methods, systems, and devices described herein can facilitate quick detection and identification of changes in the patient's condition, thereby facilitating quick, effective treatment of the patient.

In one embodiment, a display can be configured to show a display screen that includes information related to a physiological parameter being measured from a patient. The information can include a current value based on values of the physiological parameter gathered from the patient over a period of time. Examples of the current value include an average of gathered values, an average of a calculated index (e.g., an average of peak gathered values, an average of a rate of change of the gathered values, etc.), a median of gathered values, a rate of change of gathered values, a correlation (e.g., PRx, RAP index, autocorrelation, an average of autocorrelation, etc.), a maximum value among the gathered values, a minimum value among the gathered values, a root mean square (RMS), peak-to-peak values, etc. The display screen can indicate whether the current value is within a predetermined normal range for the physiological parameter. The normal range can generally indicate values of the physiological parameter that are not a cause for concern, e.g., the patient is stable and does not need immediate assessment and/or treatment change. If the current value moves outside the normal range, e.g., falls below a lower limit of the normal range or rises above an upper limit of the normal range, an alarm can be triggered. The alarm can include any one or more alarms, such as a flashing symbol shown on the display screen, a color change on the display screen, a lit-up light near the display screen, an audible sound at a nurse's station outside a room that has the patient and the display screen therein, a page to an attending physician, etc.

The display screen can also indicate whether the current value is within a predetermined goal range for the physiological parameter. The goal range can generally indicate a targeted range of values within the normal range that reflect the physiological parameter being optimally stabilized within the normal range. The goal range can thus be fully contained within the normal range, e.g., the goal range can delimit the normal range. The normal range and the goal range can thus cooperate to provide on the display screen a more complete picture of the physiological parameter for the patient.

The display screen can indicate whether the current value is within the goal range by displaying a goal indicator thereon. The goal indicator can be adjacent the current value displayed thereon and can be, e.g., a highly color-contrasted portion of the display screen, a symbol shown on the display screen, a lit-up light near the display screen, etc. If the current value moves outside the goal range, e.g., falls below a lower limit of the goal range or rises above an upper limit of the goal range, a goal alarm can be triggered. In an exemplary embodiment, the goal alarm can include removing the goal indicator from the display screen. In this way, an attending nurse and/or other medical personnel can look at the display screen and quickly determine based on presence or absence of the goal indicator whether or not the patient's physiological parameter is within the goal range. By seeing the goal indicator and thus knowing that the patient's physiological parameter is within the goal range, the attending nurse and/or other medical personnel can be assured that the physiological parameter is not reflecting a need for the attending nurse and/or other medical personnel to examine or otherwise assess the patient's condition. Similarly, if the goal indicator is not shown on the display screen, the attending nurse and/or other medical personnel can quickly determine that the patient may need attention and can consequently quickly decide to take a closer look at the patient's condition, e.g., by checking the numerical current value of the physiological parameter on the display screen, by taking a current assessment of the patient (e.g., temperature, blood pressure, etc.), by checking other information displayed on the display screen, etc. The attending nurse and/or other medical personnel can thus quickly assess patient status by viewing the display screen and without having to evaluate actual parameter values, e.g., no numerical values need be known to or evaluated by the attending nurse and/or other medical personnel to identify the patient's status. Quickly assessing the patient in this way can allow the attending nurse and/or other medical personnel to perform other job tasks (e.g., moving on to check on another patient) and/or can allow the patient to be treated before the patient's condition further deteriorates, e.g., before the physiological parameter's average has a chance to move outside the normal range.

The goal indicator can be sufficiently visually discernible on the display screen from a distance, e.g., by being large and/or highly color-contrasting. The attending nurse and/or other medical personnel thus need not get as close to the display screen as is typically done when viewing a medical monitor, and/or the attending nurse and/or other medical personnel need not even go into the patient's room, get close to the patient, and/or assess the patient's condition as related to the physiological parameter because the goal indicator can be visible from the room's door and/or at another relatively large distance. Therefore, time can be spent on other job tasks and/or in treating patients with more time-sensitive needs, room clutter can be reduced by having fewer people entering the patient's room if the display is located therein, and/or chances of patient infection can be reduced by having fewer people entering the patient's room if the display is located therein. The goal indicator can be silent, which can facilitate having a quiet care setting, which can generally make a hospital or other medical care facility less stressful and/or can help patients rest and recover.

The physiological parameter can include any one or more variables that can be monitored from a patient, as will be appreciated by a person skilled in the art. If a display screen shows current values for a plurality of physiological parameters, the display screen can indicate whether or not each one of the physiological parameters is within its own predetermined normal range, e.g., can trigger an alarm if any one of the physiological parameters falls outside its associated predetermined normal range, and whether or not each one of the physiological parameters is within its own predetermined goal range, e.g., can trigger a goal indicator to be removed from the display screen if any one of the physiological parameters falls outside its associated predetermined goal range. The one or more physiological parameters monitored from a patient can vary due to one or more factors such as medical context (e.g., neurological, cardiac, neonatal, etc.), available supplies, doctor preference, etc. Examples of physiological parameters include intracranial pressure (ICP), mean arterial blood pressure (MAP), cerebral perfusion pressure (CPP), oxygen saturation ($pO_2$) (which can be obtained by, e.g., using an invasive oxygen sensor or a pulse oximeter) such as oxygen saturation in brain tissue (PbO2), heart rate, temperature, pressure reactivity index (PRx), pressure-volume compensatory reserve (RAP) index, fluid pressure in an implantable restriction device (e.g., a gastric band, etc.), flow rate through an implantable valve (e.g., a cerebral shunt valve, etc.), gastric pH level, EEG, tissue impedance, etc. In a neurological context, exemplary monitored physiological parameters include ICP, CPP, MAP, PbO2, heart rate (HR), and brain temperature (Tb).

The displays described herein can be realized as part of virtually any device, e.g., a monitoring device, a personal computer, a workstation, a handheld computer, a tablet computer, a smartphone, or other computing device. The device can include processing circuitry configured to receive data from one or more sensors configured to gather physiological data from a patient, configured to compare sensor data to stored predetermined ranges, etc. A wide variety of displays, such as cathode ray tubes (CRTs), liquid crystal display (LCD) screens, touchscreens, etc., can be configured to display screens in response to a signal received from the processing circuitry, as a person skilled in the art will appreciate. Moreover, a wide variety of software packages can be executed on the device and/or used to develop the screens and other elements, including, for example, Flash Macromedia or custom software.

Figure 2:
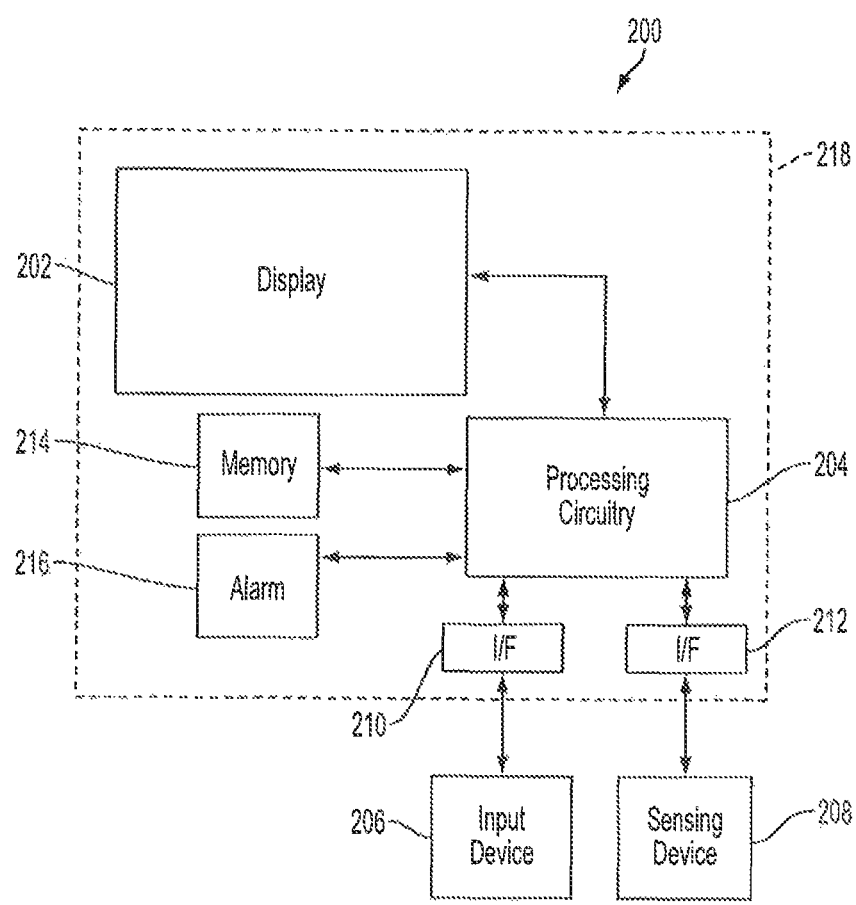
FIG. 2 is a schematic diagram of one embodiment of a device for providing a user interface on a display of the device.

FIG. 2 shows an exemplary embodiment of a device (e.g., a medical monitoring device) that can include a display screen configured to show information. The device 200 can include one or more displays 202 configured to show screens such as those described herein. The display(s) 202 can be configured to receive signals from processing circuitry 204, which can include a processor, a video card, and/or virtually any type of electronic circuitry. The processing circuitry 204 can be configured to execute software to draw appropriate screens in response to data from one or more input devices 206, e.g., representing user input, and/or data from one or more sensing devices 208. The input device(s) 206 can include devices configured to provide an input to the device 200 such as pointing devices, keyboards, buttons, microphones, soft-keys, touchscreens, etc. The input device(s) 206 can be configured to be communicatively coupled to the processing circuitry 204 via a device interface 210. The sensing device(s) 208 can include devices configured to sense and report on a physiological parameter. Examples of the sensing device(s) 208 include ICP transducers, temperature sensors, blood pressure monitors, pulse oximeters, evoked potentials, etc. The sensing device(s) 206 can be configured to be communicatively coupled to the processing circuitry 204 via a device interface 212. A memory 214 can be configured to be coupled to the processing circuitry 204 and be configured to store data, such as monitoring software, data from the sensing device(s) 208, predetermined ranges, patient data, etc. The device 200 can include an alarm mechanism 216 configured to providing an alarm, e.g., a visual alarm, an auditory alarm, a textual alarm, etc.

In an exemplary embodiment, a housing 218 of the device 200 can house, e.g., have disposed therein and/or have attached thereto, the display(s) 202, the memory 214, the alarm 216, the processing circuitry 204, and the interfaces 210, 212. In this way, the device 200 can be a self-contained unit. The device 200 can thus be portable, wireless, and/or easily connected to wired power supplies in a variety of different locations. The elements included in the housing 218 can vary. For example, although shown in FIG. 2 as separate devices, e.g., not included a housing 218 having the display(s) 202, the memory 214, the alarm 216, the processing circuitry 204, the interfaces 210, 212 disposed therein, the input devices 206 and sensing devices 208 can be integrated into the device 200, e.g., included the hosing 218. Additionally, although the display(s) 202 are shown in FIG. 2 as being integrated with the device 200, e.g., attached to the housing 218, one or more of the display(s) 202 can be separate from the device 200.

Figure 3:
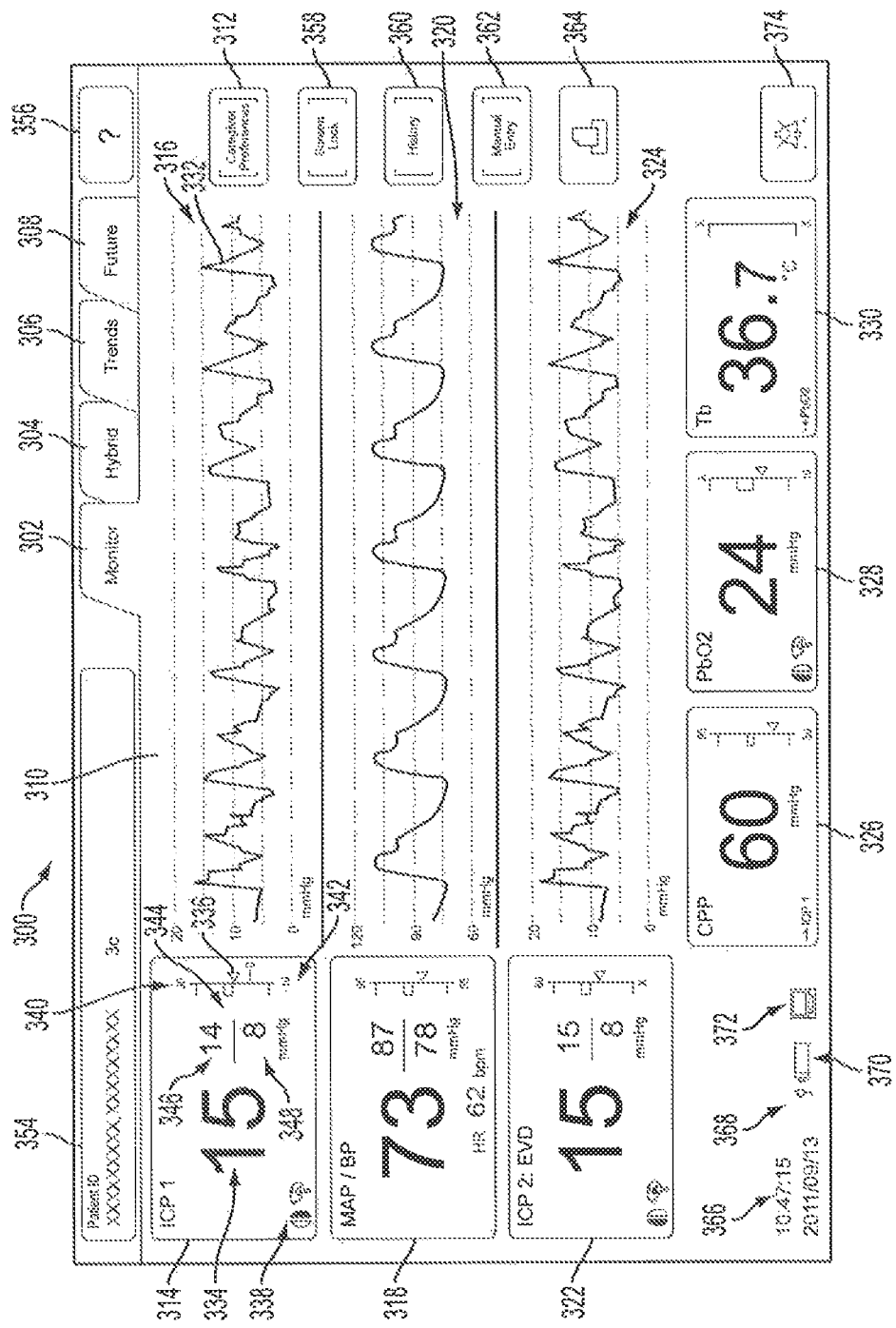
FIG. 3 is an embodiment of a monitor window of a medical monitoring system, the monitor window showing current information for a plurality of physiological parameters.

FIG. 3 shows an exemplary embodiment of a display screen 300 of a monitoring device configured to display medical information related to a patient. The display screen 300 can generally be configured as a user interface of a medical monitoring system. The display screen 300 can include a plurality of tabs, each of the tabs corresponding to a certain type or arrangement of information related to the patient. A display screen can be configured to only show one type or arrangement of information related to a patient, in which case the display screen can lack tabs. Each of the tabs can be configured to be selected by a user so as to display the tab's corresponding type or arrangement of information. In the illustrated embodiment, the display screen 300 includes a monitor tab 302, a hybrid tab 304, a trends tab 306, and a future tab 308, but the display screen 300 can include more or less than four tabs. The monitor tab 302 is selected in FIG. 3 so as to show a monitor window 310 on the display screen 300. The hybrid, trends, and future tabs 304, 306, 308 can each be selected so as to show, respectively, a hybrid window, a trends window, and a future window on the display screen 300, as discussed further below.

The monitor window 310 can be configured to show information based on one or more physiological parameters in a current time period. The current time period can be a predetermined amount of time that can be a default, preprogrammed time period, e.g., preprogrammed into a processor, or can be customized for a particular patient. The current time period can be, e.g., in a range of about five to sixty seconds, in a range of about five to ten seconds, a single heartbeat, the most recent few heartbeats of the patient, etc. The current time period can be adjustable. In some embodiments, to receive user input of this nature, the medical monitoring device can include or be configured to couple to an input device, such as a touchscreen, keypad, touchpad, pointing device, mouse, button, knob, dial, etc. As in the illustrated embodiment, the display screen 300 can include a touchscreen configured to allow the current time period to be adjusted when a user activates a caregiver preferences menu or soft button 312. Adjustment of the current time period can allow for various clinical protocols, as such protocols that can require tracking of a parameter over different time periods. Trend time periods, future time periods, normal ranges, and goal ranges for the various physiological parameters, discussed further below, can be similarly adjusted.

In the illustrated embodiment, the monitor window 310 shows current information for ICP, MAP/BP, HR, external ventricular drainage (EVD) ICP (e.g., an ICP measurement performed with an external fluid coupled sensor that is connected to the EVD system) shown as "ICP 2: EVD," CPP, PbO2, and Tb, but as mentioned above, any one or more parameters can be monitored and/or calculated, and information for any one or more type of current values based on the physiological parameters can be shown on the monitor window 310. The information displayed can be based on data received by the monitoring device in any of a variety of ways, as will be appreciated by a person skilled in the art, e.g., via a Codman Microsensor ICP Transducer (available from Codman & Shurtleff, Inc. of Raynham, Mass.), via an Integra Camino® ICP Transducer (available from Integra LifeSciences Corporation of Plainsboro, N.J.), via a blood pressure monitor, via a temperature sensor attached to the patient, etc.

For each of the physiological parameters, the monitor window 310 can be configured to show a textual display of parameter information for the current time period and/or a graphical display of parameter information for the current time period. In the illustrated embodiment, the monitor window 310 includes a textual display 314 and a graphical display 316 for ICP, a textual display 318 and a graphical display 320 for MAP/BP and HR, a textual display 322 and a graphical display 324 for EVD ICP, a textual display 326 for CPP, a textual display 328 for pbO2, and a textual display 330 for Tb. Which one or more of the physiological parameters have a textual display only, have a graphical display only, or have both a textual display and a graphical display can be user-adjusted, such as by dragging and dropping displays on the touchscreen or activating the preferences button 312.

In some instances, data may not be received for a certain physiological parameter, such as if a sensing device for the certain physiological parameter is not attached to the patient or if a sensing device for the certain physiological parameter attached to a patient has not been electronically connected to a processor that processes data to be displayed on the display screen 300. If data is not received for one or more physiological parameters, textual and graphical display(s) for those one or more physiological parameters can be absent from the monitor window 310, both the textual display(s) and the graphical display(s) for those one or more physiological parameters can be present on the monitor window 310 but lack any numerical or graphed data, or one of the graphical display(s) and textual display(s) for those one or more physiological parameters can be absent from the monitor window 310 while the other of the graphical display(s) and textual display(s) for those one or more physiological parameters can be present on the monitor window 310. By having at least one of the textual display(s) and the graphical display(s) for those one or more parameters present on the monitor window 310, it can be easier for a user observing the monitor screen 310 to determine, based on a lack of data in those graphical and/or textual display(s), that those one or more parameters are not being monitored or that the sensing device(s) for those one or more parameters are not properly configured. The present textual and/or graphical display(s) for those one or more parameters can each include at least one data absence indicator, e.g., a textual message, a warning symbol, etc., indicating that data is not being received.

Figure 4:
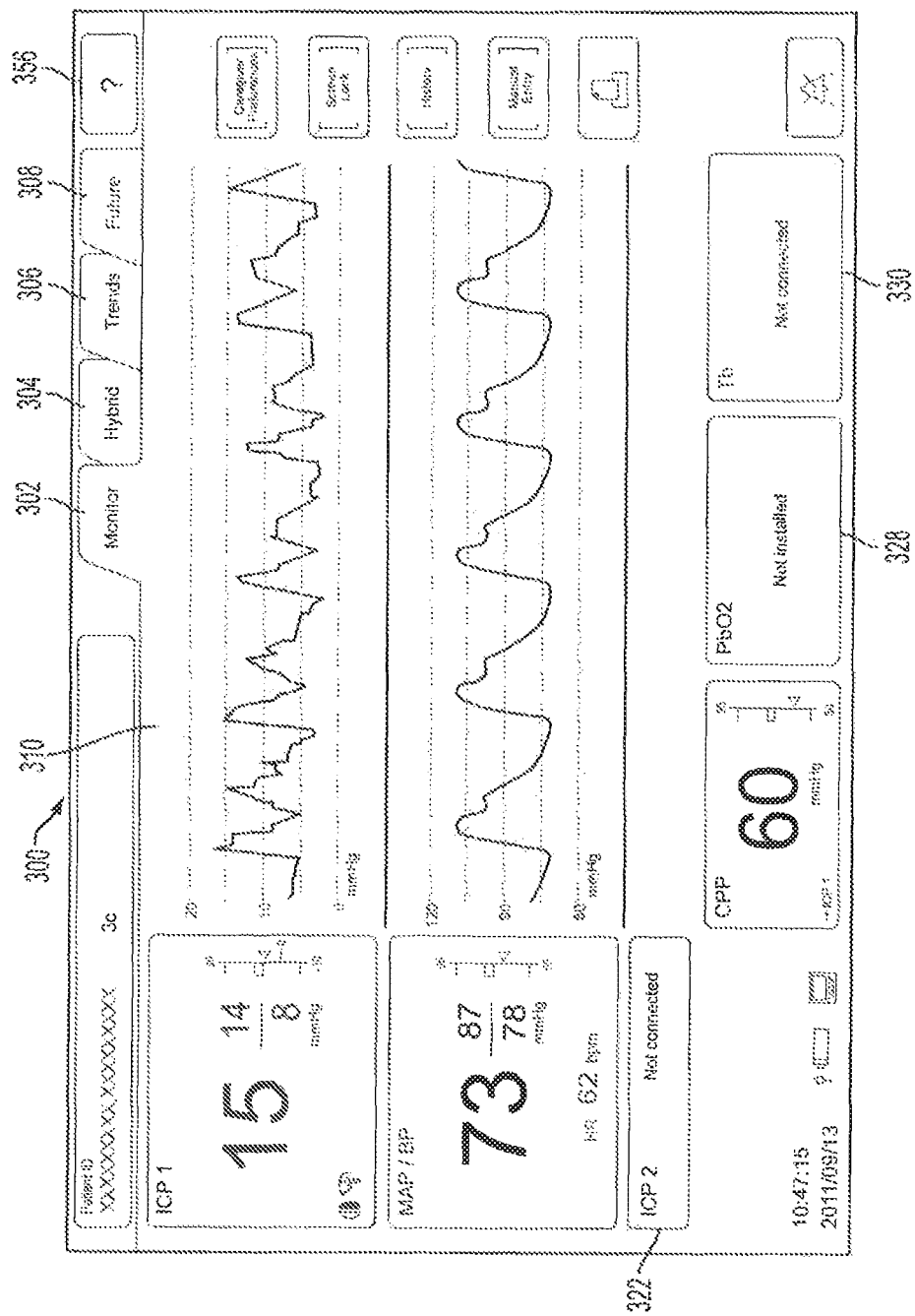
FIG. 4 shows the monitor window of FIG. 3 including current information for a subset of the physiological parameters.

FIG. 4 shows an example of the monitor window 310 in which data is being received for a plurality of physiological parameters, e.g., ICP, MAP/BP and HR, and CPP, and is not being received for another plurality of physiological parameters, e.g., EVD ICP, PbO2, and Tb. The monitor window 310 in this illustrated embodiment thus lacks graphical displays for EVD ICP, PbO2, and Tb and lacks any numerical data in the textual displays 322, 328, 330 for EVD ICP, PbO2, and Tb. In the illustrated embodiment, the textual displays 322, 328, 330 for EVD ICP, PbO2, and Tb each include a data absence indicator in the form of a textual message, "Not connected" in the EVD ICP and Tb displays 322, 330 and "Not installed" in the PbO2 display 328.

Figure 5:
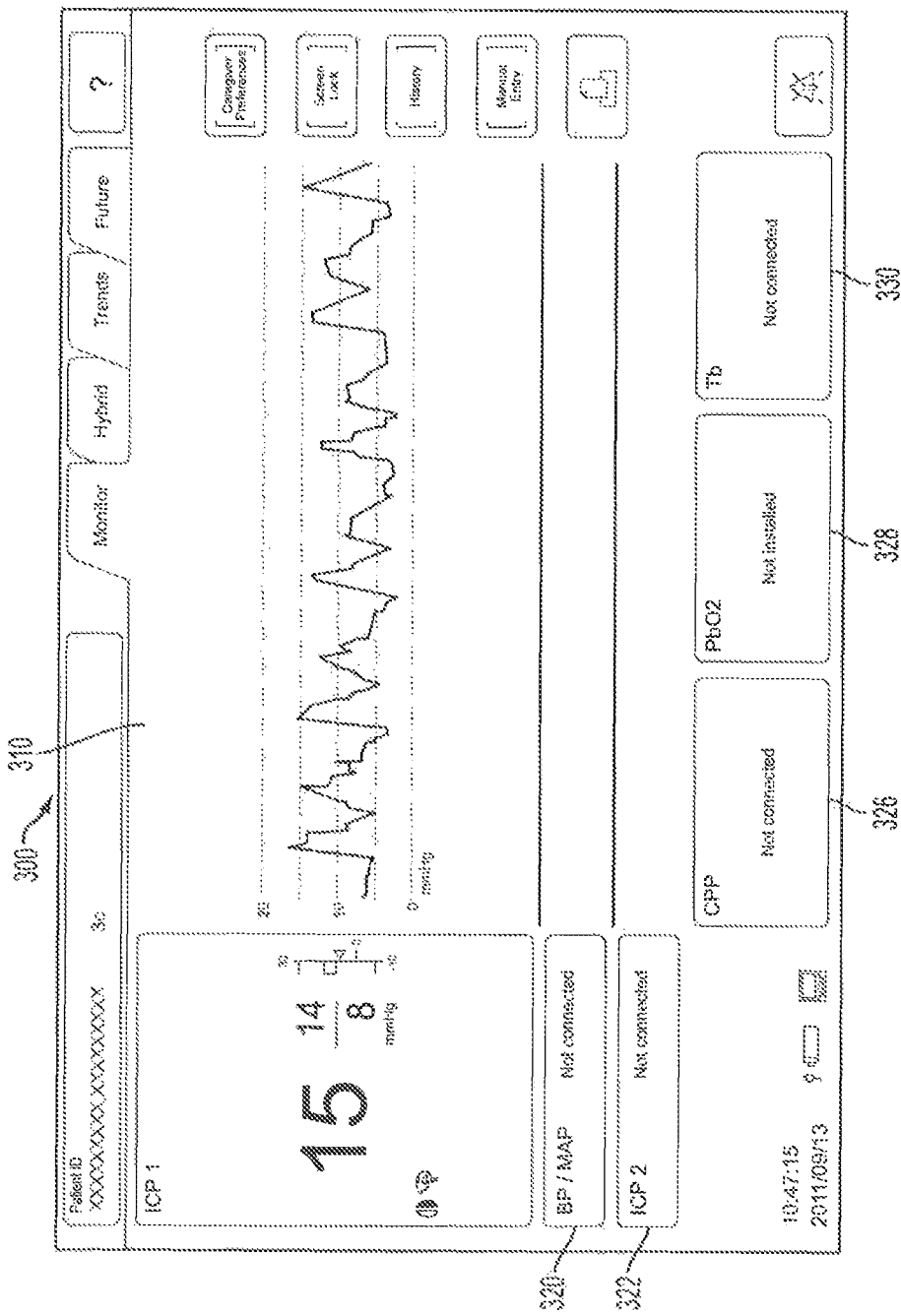
FIG. 5 shows the monitor window of FIG. 3 including current information for another subset of the physiological parameters.

FIG. 5 shows an example of the monitor window 310 in which data is being received for a single physiological parameter, e.g., ICP, and is not being received for a plurality of physiological parameters, e.g., MAP/BP and HR, CPP, EVD ICP, PbO2, and Tb. The monitor window 310 in this illustrated embodiment thus lacks graphical displays for MAP/BP and HR, CPP, EVD ICP, PbO2, and Tb and lacks any numerical data in the textual displays 320, 322, 326, 328, 330 for MAP/BP and HR, CPP, EVD ICP, PbO2, and Tb. In the illustrated embodiment, the textual displays 320, 322, 326, 328, 330 for MAP/BP and HR, CPP, EVD ICP, PbO2, and Tb each include a data absence indicator in the form of a textual message, "Not connected" in the MAP/BP and HR, EVD ICP, CPP, and Tb displays 320, 322, 326, 330 and "Not installed" in the PbO2 display 328.

Referring again to FIG. 3, the textual display for each physiological parameter can include numerical data regarding the physiological parameter for the current time period, and the graphical display for each physiological parameter can include a graphical illustration of the numerical data for the current time period. For ease of discussion, the textual display 314 and the graphical display 316 for ICP are discussed below as representative examples of textual and graphical displays for a physiological parameter shown on the monitor window 310. Textual and graphical displays for other physiological parameters shown on the monitor window 310 can be similarly configured. Additionally, ICP is shown in the ICP textual and graphical displays 314, 316 in units of mmHg, but ICP can be displayed in any appropriate unit. Similarly, other physiological parameters shown on the monitor window 310 can be displayed in any appropriate units.

The graphical display 316 can represent ICP graphically with a waveform or graph line 332 plotted over the current time period. However, virtually any graphical representation can be used, such as a graph line, a bar graph, a plot of discrete data points, and/or other pictorial display. The graphical display 316 in the illustrated embodiment plots via the graph line 332 ICP values gathered and/or calculated during the current time period. However, the graphical display 316 can show (e.g., via a graph line and/or other pictorial display) values of another statistic based on ICP, e.g., a mean value of the physiological parameter calculated over a sample period, e.g., every two to three seconds, a median value, a normalized value, a systolic value, a diastolic value, wave amplitude, etc. In an exemplary embodiment, if the monitor window 310 shows information for a plurality of physiological parameters, as in the illustrated embodiment, the same statistic(s) are shown on the monitor window 310 for each of the parameters, thereby facilitating quick identification and understanding of the displayed information.

The textual display 314 can represent ICP textually and/or pictorially. In the illustrated embodiment, the textual display 314 includes information related to an average of ICP values gathered and/or calculated during the current time period including a current average (e.g., the current average intracranial pressure), a current actual value (e.g., a most recently measured and/or calculated ICP value), a normal range for the current average, and a goal range for the current average. Although a current value related to ICP is an average of gathered values in the illustrated embodiment, as mentioned above, other current values can be shown instead of or in addition to the average of gathered values, e.g., an average of a calculated index (e.g., an average of peak gathered values, an average of a rate of change of the gathered values, etc.), a median of gathered values, a rate of change of gathered values, a correlation (e.g., PRx, RAP, autocorrelation, an average of autocorrelation, etc.), a maximum value among the gathered values, a minimum value among the gathered values, a root mean square (RMS), peak-to-peak values, etc.

The current average can be shown textually and/or graphically. In the illustrated embodiment, the current average is shown textually with a numerical value 334. The average ICP value in the illustrated embodiment is 15 mmHg. As will be appreciated by a person skilled in the art, the numerical value 334 shown on the monitor window 310 can be an exact average value or can be a rounded value, e.g., rounded to a nearest whole number (as in the illustrated embodiment), rounded to one decimal place, rounded to two decimal places, etc.

The current actual value can be shown textually and/or graphically. In the illustrated embodiment, the current actual value is shown graphically with a current value mark 336 on and/or adjacent a normal range scale. The current value mark's position along the normal range scale can indicate the current actual value's numerical value. The current ICP value in the illustrated embodiment is 7 mmHg.

The normal range can be shown textually and/or graphically. In the illustrated embodiment, the normal range is shown graphically with the normal range scale. The normal range scale can have an upper normal limit 340 that corresponds to a predetermined upper limit of the normal range, and the normal range scale can have a lower normal limit 342 that corresponds to a predetermined lower limit of the normal range. In the illustrated embodiment, the upper normal limit 340 for ICP is 30 mmHg, and the lower normal limit 342 for ICP is −10 mmHg. The normal range can be predetermined based on a normal range for typical patients and can be preprogrammed into the system. Alternatively, the normal range can be predetermined by being customized for the patient, e.g., determined by a doctor treating the patient and entered into the system including the display. In an exemplary embodiment, the normal range can be preprogrammed into the system as the normal range for typical patients, thereby setting the normal range for typical patients as a default normal range. By way of example, a typical normal range for ICP is about 0 to 20 mmHg, a typical normal range for CPP is about 50 to 150 mmHg, a typical normal range for Tb is about 36 to 37.5° C., and a typical normal range for MAP is about 70 to 110 mmHg. The normal range can optionally be readjusted by a user, e.g., be customized for the patient, such as by activating the preferences button 312. In an exemplary embodiment, each of the physiological parameters can have its own predetermined normal range. Each of the predetermined normal ranges can be independent from one another. However, one or more of the predetermined normal ranges can be defined by one or more of the other predetermined normal ranges, e.g., a predetermined normal range for CPP being based on a predetermined normal range for ICP and a predetermined normal range for MAP.

The goal range can be shown textually and/or graphically. In the illustrated embodiment, the goal range is shown graphically with a goal range scale 344. The goal range scale 344 can be on and/or adjacent the normal range scale, as in the illustrated embodiment, which can facilitate comparison of the normal range and the goal range and/or can facilitate simultaneous comparison of the current ICP value, e.g., as indicated by the current value mark 336, with the normal range and the goal range. The goal range mark's position along the normal range scale can indicate the goal range. The goal range is also shown textually in the illustrated embodiment with an upper goal limit 346 that corresponds to a predetermined upper limit of the goal range and with a lower goal limit 348 that corresponds to a predetermined lower limit of the goal range. In the illustrated embodiment, the upper goal limit 346 for ICP is 14 mmHg, and the lower goal limit 348 for ICP is 8 mmHg. The goal range can be predetermined based on an optimal range within the normal range for typical patients and can be preprogrammed into the system. By way of example, a predetermined goal range for ICP can be about 5 to 15 mmHg, a predetermined goal range for CPP can be about 70 to 90 mmHg, a predetermined goal range for Tb can be about 36.5 to 37.1° C., and a predetermined goal range for MAP can be about 80 to 100 mmHg. Alternatively, the goal range can be predetermined by being customized for the patient, e.g., determined by a doctor treating the patient and entered into the system. In an exemplary embodiment, the goal range can be preprogrammed into the system as the goal range for typical patients, thereby setting the goal range for typical patients as a default goal range. The goal range can optionally be readjusted by a user, e.g., to be customized for the patient, such as by activating the preferences button 312. As shown, the goal range can be nested within the normal range, e.g., fall entirely within the normal range. In other words, the upper limit 346 of the goal range can be less than the upper limit 340 of the normal range, and the lower limit 348 of the goal range can be greater than the lower limit 342 of the normal range.

In an exemplary embodiment, each of the physiological parameters can have its own predetermined goal range. Each of the predetermined goal ranges can be independent from one another. However, one or more of the predetermined goal ranges can be defined by one or more of the other predetermined goal ranges, e.g., a predetermined goal range for CPP being based on a predetermined goal range for ICP and a predetermined goal range for MAP.

Figure 6:
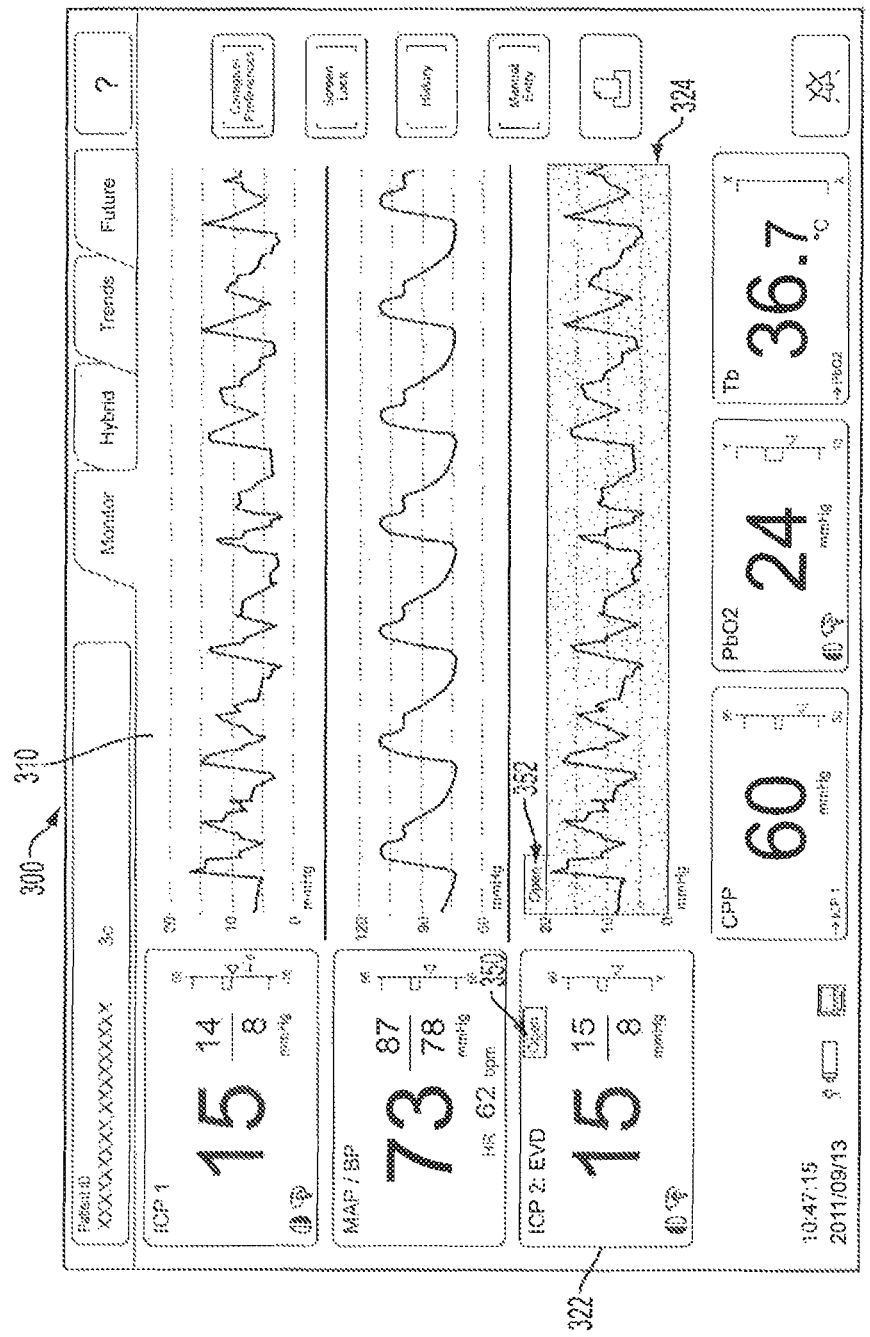
FIG. 6 shows the monitor window of FIG. 3 including an indication that an extraventricular drain related to one of the physiological parameters is in an open state.

The textual displays and/or the graphical displays for any one or more of the physiological parameters shown in the monitor window 310 can include other information regarding their respective physiological parameters. For example, still using ICP as a representative example, the textual display 314 can include a sensing device position indicator 338 that indicates a position (e.g., (L/R parenchyma, L/R ventricle, or lumbar) of a sensing device (not shown) sensing ICP from the patient so as to gather ICP values therefrom. The position can be entered manually. Although the sensing device position indicator 338 is included in the textual display 314 in the illustrated embodiment, the sensing device position indicator 338 can be included in the graphical display 316. In the illustrated embodiment, the sensing device position indicator 338 indicates that the sensing device sensing ICP is located in a right side of the patient's brain in an upper region thereof. For another example, the textual display 322 and/or the graphical display 324 for EVD ICP can indicate textually and/or graphically whether or not the EVD having the EVD ICP is an open state or a closed state. As will be appreciated by a person skilled in the art, a default state of an EVD is typically the closed state. FIG. 3 thus indicates that the EVD is in the closed state by not providing any particular textual or graphical indication regarding the EVD's open or closed state. FIG. 6 illustrates an embodiment in which the EVD is indicated as being in the open state, e.g., that the EVD opened to relieve excess cerebral spinal fluid (CSF) in the brain. The open state is indicated in the FIG. 6 embodiment with a textual EVD state indicator 350 ("Open") in the EVD textual display 314, a second textual EVD state indicator 352 ("Open") in the EVD graphical display 316, and a graphical EVD state indicator in the form of background shading in the EVD graphical display 316. The textual EVD state indicators 350, 352 can have other configurations (e.g., "open state," "EVD open," "closed," "EVD closed," etc.), and the graphical EVD state indicator can also have other configurations (e.g., a schematic illustration of an open EVD device, etc.)

Referring again to FIG. 3, the display screen 300 can include a wide variety of other features and display a wide variety of other data. The display screen 300 can include one or more static features configured to be on the display screen 300 regardless of which of the tabs 302, 304, 306, 308 is currently selected. For example, the display screen 300 can include any one or more of a patient ID window 354 that identifies the patient (e.g., by name, number, code, etc.); a help button 356 configured to be user-activated so as to provide technical assistance (e.g., access to a user manual, ability to search Frequently Asked Questions, etc.); a screen lock button 358 configured to be user-activated so as to temporarily pause or freeze the information on the currently displayed window (which is the monitor window 310 in FIG. 3), which can be advantageous for training purposes and/or to examine a particular aspect of the display in more detail; a history button 360 configured to be user-activated so as to provide historical sensed data for the patient and/or other patient records; a manual entry button 362 configured to be user-activated so as to provide access to an event marking screen for inputting marked events on the currently displayed window; a print button 364 configured to be user-activated so as to provide the ability to print the currently displayed window or portion(s) thereof (e.g., print to an attached printer or a printer integrated into the medical monitoring device); a current date/time indicator 366; a power connector 368 that indicates whether or not the device is connected to external electrical power; a charge indicator 370 that indicates a current charge of a battery included in the monitoring device; a docking indicator 372 that indicates whether or not the device is docked at a docking station (e.g., a bedside docking station, etc.); an alarm silence button 374 configured to be user-activated for acknowledging an alarm and/or silencing an audible alarm in those embodiments in which the monitoring device includes an audible alarm for indicating that the average of one or more physiological parameters is out of limit (e.g., outside the normal range, etc.); etc. Embodiments of providing historical sensed data and embodiments of marking events are described in further detail in U.S. Pat. Pub. No. 2009/0005703 entitled "Medical Monitor User Interface" filed Jun. 27, 2007, which is hereby incorporated by reference in its entirety. One or more static features may only be shown on the monitor window 310 in response to a trigger event, such as the alarm silence button 374 being configured to appear only when the an out-oflimit condition is determined, the docking indicator 372 only appearing to indicate an undocked device, etc.

The relative sizes and locations of the various windows, symbols, text, icons, etc. of the monitor window 310, and for other windows that can be shown on the display screen 300, are exemplary in nature. A person skilled in the art will appreciate that any of the various windows, symbols, text, icons, etc. of the display screen 300 can have virtually any size and virtually any location.

The textual display and/or the graphical display for each of the physiological parameters ICP, MAP/BP and HR, EVD ICP, CPP, PbO2, and Tb shown on the monitor window 310 can be configured to be observed by a user, e.g., viewed on the screen 300, so as to assess the patient's condition. To facilitate assessment of the patient's condition, an alarm can be provided if any of the physiological parameters fall outside their associated normal range. The alarm can be provided in a variety of ways.

In an exemplary embodiment, when an average of one of the physiological parameters, e.g., ICP, MAP/BP, HR, EVD ICP, CPP, PbO2, and Tb, shown on the monitor window 310 falls outside its associated predetermined normal range, the alarm can be triggered. In other words, when an average of one of the physiological parameters increases to be above the predetermined upper normal limit for that physiological parameter or decreases to be below the predetermined lower normal limit for that physiological parameter, the alarm can be triggered. In other words, when the physiological parameter's average falls outside the normal range as determined by the device's processor, the processor can cause the device's alarm to activate.

As mentioned above, the alarm can include any one or more alarms, as such as a flashing symbol shown on the display screen 300, a color change on the display screen 300, a lit-up light near the display screen 300, an audible sound at a nurse's station outside a room that has the patient and the display screen 300 therein, a page to an attending physician, etc. In an exemplary embodiment, the alarm for an out-of-normal-range physiological parameter can include at least an audible sound and a color change on the display screen 300 within the textual display for the out-of-normal-range physiological parameter. The audible sound can include any sound, as will be appreciated by a person skilled in the art, e.g., a ringing bell sound, a series of beeps, a siren sound, etc. The color change can include changing a color of at least a portion of a background of the out-of-normal-range physiological parameter's textual display.

In an exemplary embodiment, a majority portion of the background of the out-of-normal-range physiological parameter's textual display can change from a first color to a second, different color in response to the physiological parameter's average moving out of the normal range. Color is generally easily discernable even from a relatively large distance, e.g., at a distance from a door of a patient's room to the display screen within the patient's room. The alarm can thus be easily detected from a relatively large distance, even if the alarm does not include a traveling audible sound. The second color can highly contrast with the first color, which can help highlight the color change by allowing the second color to be clearly visible as an atypical color on the screen 300, and hence be indicative of a special condition, e.g., an out-of-normal-limit parameter. Examples of exemplary first color/second color pairs include black/white, black/red, white/red, black/yellow, a color on one side of the color wheel/a color directly opposite the color on the color wheel, grey/red, etc. The first and second colors can each be any color, and can be solid, patterned, flashing, textured, etc.

In an exemplary embodiment, the first color can be non-flashing, and the second color can be flashing, e.g., alternating between at least two different colors (e.g., at least two colors each highly contrasting with the first color). The first color can be the same for all of the textual displays on the display screen 300, which can facilitate identification of any out-of-normal-range parameters. In the illustrated embodiment, as shown in FIG. 3, each of the textual displays 314, 318, 322, 326, 328, 330 has a background of a first color, which in the illustrated embodiment is black. As will be appreciated by a person skilled in the art, any characters (e.g., text and/or symbols) or images within a textual display that changes from the first color to the second color, as well as from the second color to the first color, can also change color in order for the characters and images to be visible in the textual display regardless of the textual display's background color(s). Additionally, the graphical display for the out-of-normal-range parameter can change color, include an alarm symbol therein, etc., in addition to or instead of the out-of-normal-range parameter's textual display including the alarm.

Figure 7:
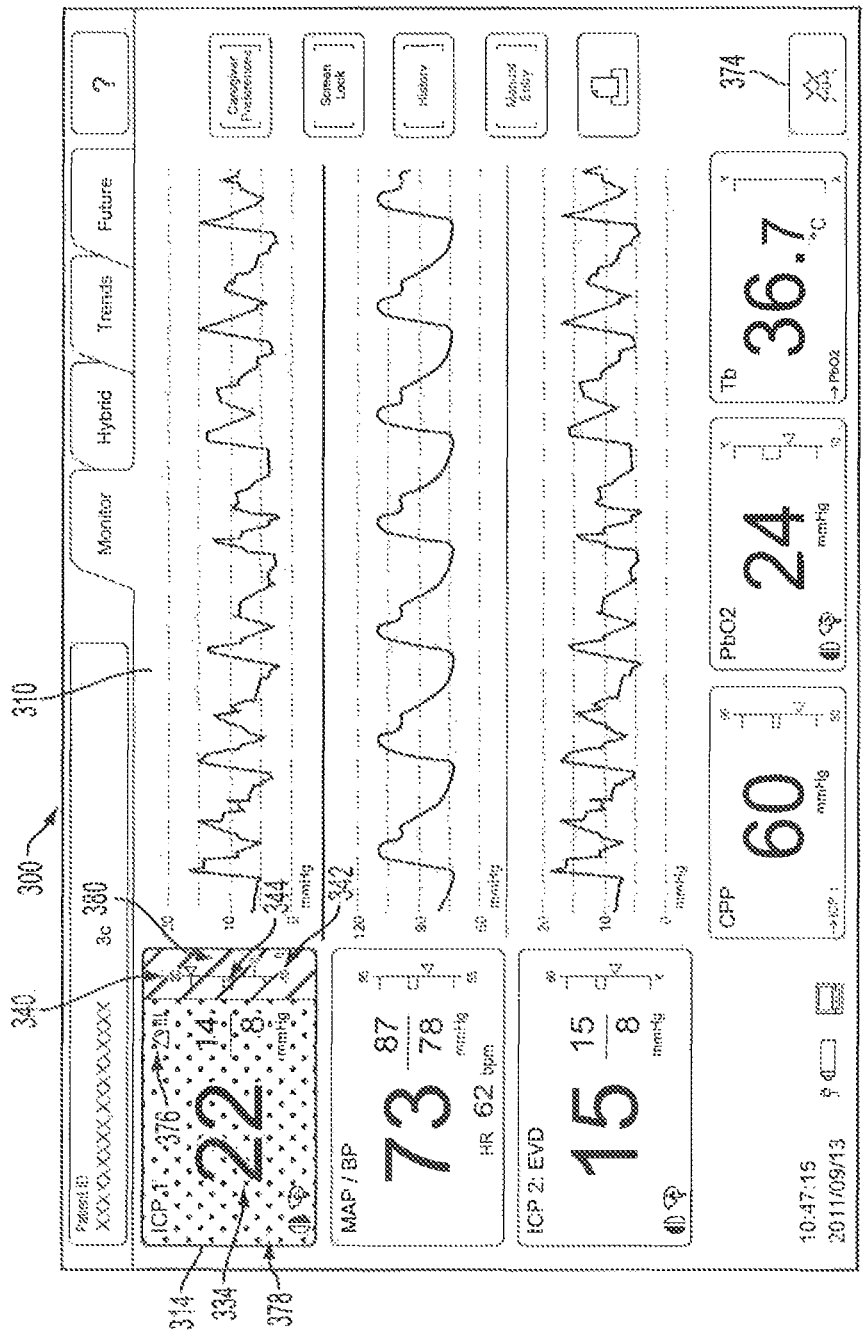
FIG. 7 shows the monitor window of FIG. 3 including an alarm for an ICP one of the physiological parameters.

FIG. 7 shows an embodiment of the display screen 300 after the average ICP falls outside its predetermined normal range, which in the illustrated embodiment is the average exceeding the upper normal limit 340, e.g., the current average value 334 of 22 mmHg being above the upper normal limit 340 of 20 mmHg. In response to the ICP average falling outside the normal range, an alarm was triggered, thereby changing a majority portion 378 of the background for the ICP textual display 314 from a first color, e.g., black, in FIG. 3 to a second color, e.g., red, in FIG. 7. The majority portion 378 in the illustrated embodiment includes a portion of the ICP textual display 314 that includes the current average value 334, the upper and lower goal limits 346, 348, and the sensing device position indicator 338. A minority portion 380 of the background for the ICP textual display 314 changed from the first color in FIG. 3 to a second color, e.g., white, in FIG. 7. The minority portion 380 in the illustrated embodiment includes a portion of the ICP textual display 314 that includes the normal range scale, the upper and lower normal range limits 340, 342 and the goal range scale 344. The display screen 300 showing an alarm for ICP in FIG. 7 in the form of a background color change also includes an alarm in the form of an alarm symbol 376 shown in the ICP textual display 314. The alarm symbol includes a warning triangle and exclamation points in the illustrated embodiment, but the alarm symbol can include any one or more of a variety of text and/or symbols, e.g., the word "alarm," a star, a bell, etc. The alarm symbol 376 is within the ICP textual display 314, e.g., within the out-of-normal-range parameter's textual display, in the illustrated embodiment, but the alarm symbol 376 can be adjacent the out-of-normal-range parameter's textual display, within the out-of-normal-range parameter's graphical display, and/or adjacent the out-of-normal-range parameter's graphical display.

In the illustrated embodiment of FIG. 7, the MAP/BP, HR, EVD ICP, CPP, PbO2, and Tb physiological parameters are within their respective normal ranges such that alarms are not shown for any of MAP/BP, HR, EVD ICP, CPP, PbO2, and Tb. Although only one alarm is shown in FIG. 7, any one or more of the parameters on the screen 300 can, in any combination thereof, have alarms therefor.

Figure 8:
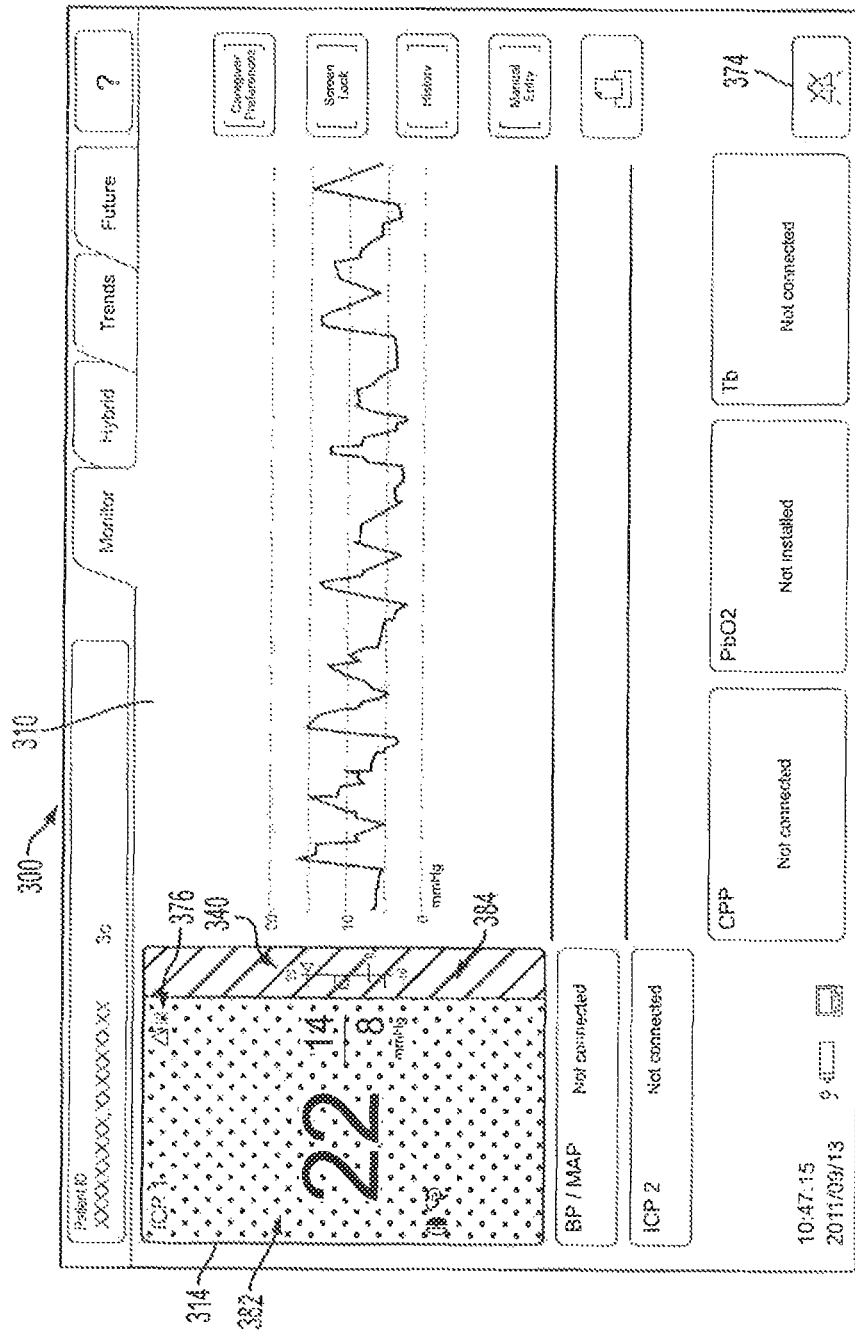
FIG. 8 shows the monitor window of FIG. 5 including an alarm for the subset of the physiological parameters.

FIG. 8 shows another embodiment of the display screen 300 after the average ICP falls outside its predetermined normal range, which in the illustrated embodiment is the average exceeding the upper normal limit 340, e.g., the current average value 334 of 22 mmHg being above the upper normal limit 340 of 20 mmHg. FIG. 8 shows the alarm being triggered from the monitor window 310 of FIG. 5 in which data is being received for a single physiological parameter, ICP. The alarm in FIG. 8 includes, similar to FIG. 7, a majority portion 382 of the background color of the ICP textual display 314 changing colors (black to red), a minority portion 384 of the background color of the ICP textual display 314 changing colors (black to white), and the alarm symbol 376 being present within the ICP textual display 314.

The ICP average decreasing below the lower normal limit 342 and the other physiological parameters on the screen 300 falling outside their respective normal ranges can trigger an alarm similar to that discussed with respect to the ICP alarms of FIGS. 7 and 8.

A duration of the alarm can be determined and stored, e.g., in a storage unit, which can facilitate evaluation of the patient's condition, e.g., if displayed on the screen 300. In other words, start and stop times of the alarm can be saved.

When an alarm is triggered, the alarm can persist, e.g., a sound can continue sounding, the textual display's background color can remain the second color, the textual display's background color can flash, a warning light attached to the display can continue flashing, etc., until the alarm is acknowledged by a user and/or until the out-of-normal range parameter's average falls back within the normal range. The alarm can be acknowledged in a variety of ways, such as by activating the alarm silence button 374. In an exemplary embodiment, the alarm silence button 374 can appear only when an alarm is triggered.

When the alarm is acknowledged, the display screen 300 can continue to indicate that the out-of-normal-range parameter is outside the normal range until the parameter returns to within the normal range. In this way, the display screen 300 can indicate that the alarm condition has been observed by at least one medical practitioner, e.g., nurse, doctor, etc. Thus, any subsequent observer of the display screen 300 while the alarm condition persists can determine from the display screen 300 that the alarm has been previously observed and is likely being tended to as needed. The display screen 300 can display an acknowledged alarm in a variety of ways. In an exemplary embodiment, the acknowledged alarm for an out-of-normal-range physiological parameter can include at least a color change on the display screen 300 within the textual display for the out-of-normal-range physiological parameter. The portion(s) of the out-of-range parameter's textual display that changed to indicate the alarm can change again similar to that discussed above regarding the change from the first color to the second color, e.g., change from the second color to a third color that is different from the first color and the second color. The change to the third color can be similar to that discussed above regarding the change from the first color to the second color. The third color can highly contrast with each of the first color and the second color, which can help highlight the color change by allowing the third color to be clearly visible as an atypical color on the screen 300, and hence indicative of a special condition, e.g., an acknowledged out-of-normal-limit parameter. Examples of exemplary first color/second color/third color trios include black/white/red, black/red/white, white/red/black, black/yellow/red, the three primary colors, etc. The third color can be any color, and can be solid, patterned, flashing, textured, etc. In an exemplary embodiment, the second color can be solid and non-flashing, and the third color can be a non-flashing pattern including a same color as the second color. e.g., a second color being red and a third color being stripes in the second color and another color. The third color can be the same for all of the textual displays on the display screen 300, which can facilitate identification of any acknowledged out-of-normal-range parameters.

Figure 9:
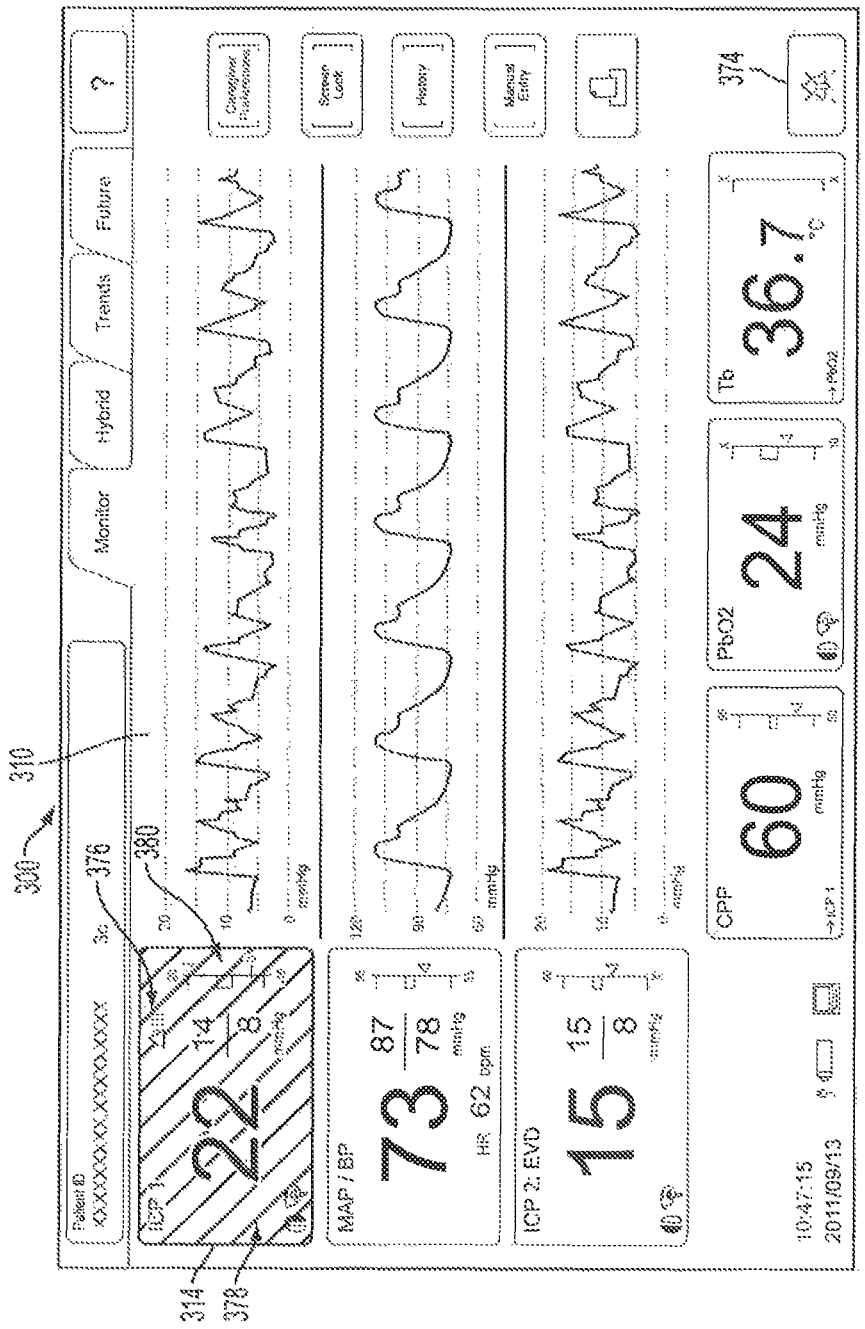
FIG. 9 shows the monitor window of FIG. 7 including an alarm acknowledgement for the ICP one of the physiological parameters.

FIG. 9 shows an embodiment of the display screen 300 after acknowledgement of the alarm of FIG. 7. In response to the alarm being acknowledged, e.g., in response to activation of the alarm silence button 374, an acknowledgement was triggered, thereby changing the majority portion 378 of the background for the ICP textual display 314 from the second color, e.g., red, in FIG. 7 to a third color, e.g., white, in FIG. 9. The minority portion 380 of the background for the ICP textual display 314 did not change from FIG. 7 to FIG. 9. The alarm symbol 376 can remain present on the display screen 300 even after the alarm has been acknowledged, as shown in FIG. 9.

Similar to that discussed above regarding the alarm for the normal range, to facilitate assessment of the patient's condition, a goal alarm can be provided if any of the physiological parameters are outside their associated goal range. In an exemplary embodiment, the goal alarm can be provided for a physiological parameter when the physiological parameter is outside its associated goal range and is within its associated normal range. The goal alarm can indicate to medical personnel, e.g., an attending nurse, a doctor, etc., that the patient may need assessment and/or treatment because the physiological parameter associated with the goal alarm is not in an optimal range and therefore may be heading outside its normal range. In other words, the patient's condition may be deteriorating but can be assessed and/or the patient can be treated prior to the patient being in a more dire condition. The goal alarm can thus function in a preventative way. The goal alarm can be provided in a variety of ways.

In an exemplary embodiment, when an average of one of the physiological parameters, e.g., ICP, MAP/BP, HR, EVD ICP, CPP, PbO2, and Tb, is within its associated predetermined goal range, and hence is also within its associated normal range, a goal indicator can be shown on the display screen 300. In other words, when an average of one of the physiological parameters is within its associated goal range, e.g., below its associated predetermined upper goal limit and above its associated predetermined lower goal limit, the goal indicator can be triggered to be displayed on the screen 300 for that physiological parameter. The device's processor can be configured to determine whether the physiological parameters' averages are within their respective the goal ranges and can be configured to cause the goal indicator to be shown on the screen 300. The statuses of the physiological parameters shown on the display screen 300 can thus be quickly assessed by checking the display screen 300, e.g., by a user looking at the display screen, to determine if a goal indicator is present on the screen 300 for each of the physiological parameters. The goal alarm for a physiological parameter can, in an exemplary embodiment, include absence of the goal indicator from the screen 300 for that physiological parameter.

Based on the presence of a goal indicator on the screen 300 for a physiological parameter, a medical practitioner need not examine actual numerical values on the display screen 300 for the parameter having the goal indicator associated therewith to determine that that parameter is within an acceptable range, thereby saving time and/or helping to reduce errors in determining whether the patient's measured parameters are within an acceptable range. A goal indicator being present on the screen 300 for each of the physiological parameters can indicate that each of the parameters is within its associated goal range, thereby indicating that the physiological parameters point to the patient being in relatively good condition. A medical practitioner can thus conclude based on the presence of the goal indicators for all of the parameters that the patient need not be assessed and/or treated at this time. The medical practitioner can, however, nevertheless determine to assess and/or treat the patient at this time based on any other number of factors, such as to maintain a regular schedule of patient assessments.

Correspondingly, based on the absence of a goal indicator from the screen 300 for a physiological parameter, the medical practitioner need not examine actual numerical values on the display screen 300 for the parameter not having a goal indicator associated therewith to determine that the parameter is not within an acceptable range, thereby saving time and/or helping to reduce errors in determinations of whether the patient's measured parameters are within an acceptable range. A goal indicator not being present on the screen 300 for any of the physiological parameters can indicate that none of the parameters are within their associated goal ranges. No goal indicators and no normal range alarms being present on the screen 300 for any of the parameters can indicate that despite the patient's physiological parameters being within their respective normal ranges, assessing and/or treating the patient at this stage may be advisable, e.g., to help prevent the patient's condition from deteriorating outside the normal range of any of the physiological parameters. A medical practitioner can thus conclude based on the presence of the goal indicators for none of the parameters that the patient should be assessed and/or treated at this time. The medical practitioner can, however, nevertheless determine to not assess and/or treat the patient at this time based on any other number of factors, such as to first allow for consultation with colleague(s). Similarly, a goal indicator not being present on the screen 300 for at least one but less than all of the physiological parameters can indicate that at least one of the parameters its outside its associated goal range and that assessing and/or treating the patient at this stage may be advisable.

The goal indicator can be provided in a variety of ways. The goal indicator can include any one or more indicators, such as a highly color-contrasted portion of the screen, a symbol shown on the display screen, a lit-up light near the display screen, etc. In an exemplary embodiment, the goal indicator can be visually discernable and silent, e.g., non-audible, which can allow the goal indicator to be non-intrusively provided. The goal indicator can be shown on the display screen 300 adjacent its associated physiological parameter displayed on the screen 300, which can facilitate associating a goal indicator with its associated physiological parameter among a plurality of parameters shown on the screen 300. In an exemplary embodiment, the goal indicator for an in-goal-range physiological parameter can include at least a color change on the display screen 300 within the textual display for the in-goal-range physiological parameter. The color change can include changing a color of at least a portion of a background of the in-goal-range physiological parameter's textual display. In an exemplary embodiment, a minority portion of the background of the in-goal-range physiological parameter's textual display can change from a first color to a second, different color in response to the physiological parameter's average being within the goal range. As mentioned above, color is generally easily discernable even from a relatively large distance. The goal indicator can thus be easily observed from a relatively large distance, even if the goal indicator does not include any audible sound. The second color can highly contrast with the first color, as discussed above within respect to the alarm for out-of-normal-range parameters, which can help highlight the color change by allowing the second color to be clearly visible as an atypical color on the screen 300, and hence indicative of a special condition, e.g., an in-goal-limit parameter. The first and second colors can vary, as discussed above regarding the alarm for an out-of-normal-limit parameter. Also similar to that discussed above, the graphical display for the in-goal-range parameter can change color, include a goal indicator symbol therein, etc., in addition to or instead of the in-goal-range parameter's textual display.

The goal indicator can optionally include a trend indicator that indicates whether its associated physiological parameter's average is increasing or decreasing. The trend indicator can reflect an increasing or decreasing trend of the physiological parameter over the current time period or over another time period, e.g., one hour, twenty-four hours, a trend time period discussed further below, a time period corresponding to an attending medical practitioner's shift, etc. The trend indicator indicating a trend corresponding to the trend time period can allow trends information to be accessible on the monitor window 310 without having to switch to the hybrid window or the trends window, both discussed further below. The trend indicator can have a variety of configurations. Examples of the trend indicator include an arrow that points up to indicate an increasing average trend or that points down to indicate a decreasing average trend; a textual message of "rising," "increasing," etc. to indicate an increasing average trend or "falling," "decreasing," etc. to indicate a decreasing average trend; etc. The trend indicator can be positioned within and/or adjacent to its associated physiological parameter's textual display. In an exemplary embodiment, the trend indicator can positioned within the goal indicator within the associated physiological parameter's textual display, e.g., an arrow within a goal indicator color in the textual display.

Figure 10:
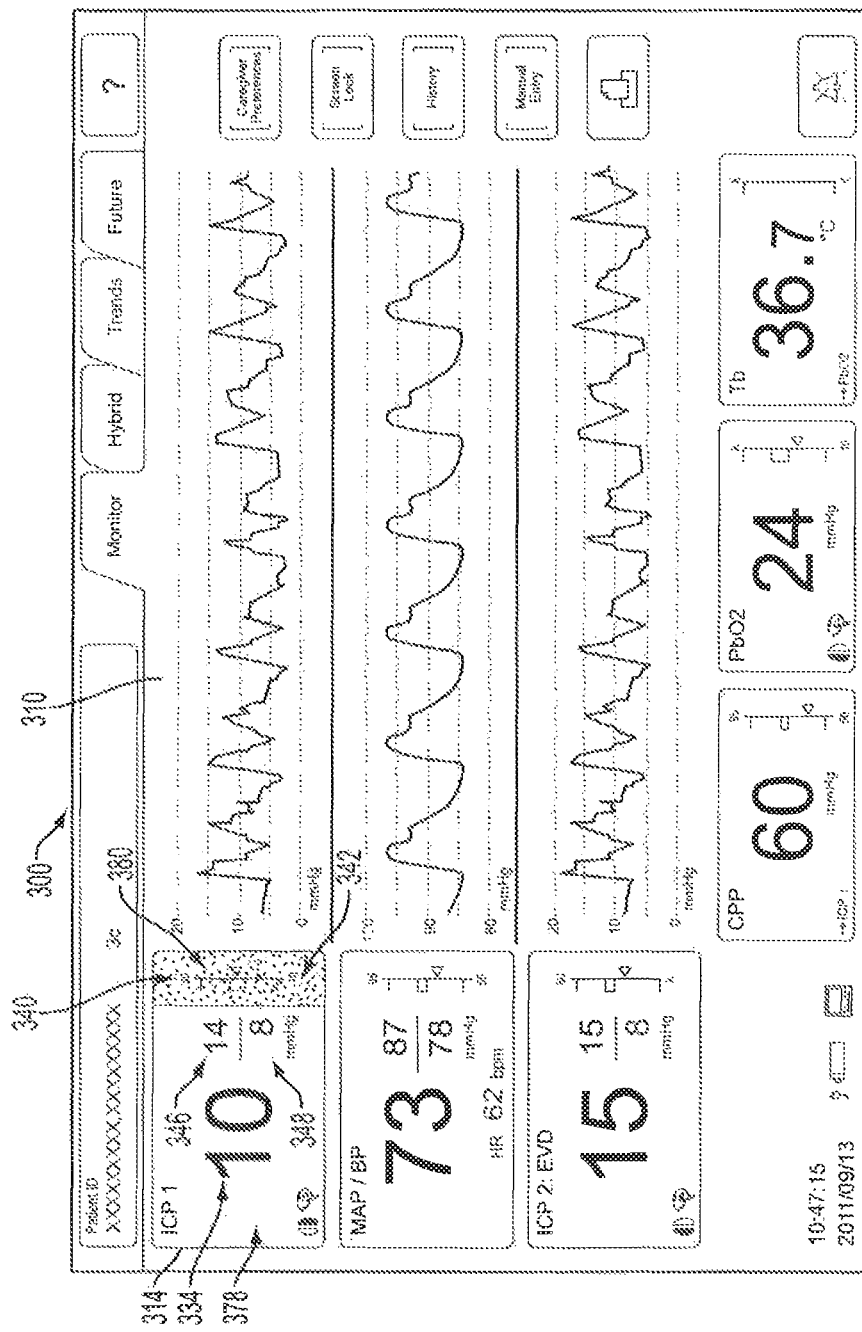
FIG. 10 shows the monitor window of FIG. 3 including a goal indicator for an ICP one of the physiological parameters.

FIG. 10 shows an embodiment of the display screen 300 when the average ICP is within its predetermined goal range, which in the illustrated embodiment is the average being less than the upper goal limit 346, being less than the upper normal limit 340, being greater than the lower goal limit 348, and being greater than the lower normal limit 342, e.g., the current average value 334 of 10 mmHg being less than the upper goal limit 346 of 14 mmHg, being less than the upper normal limit 340 of 20 mmHg, being greater than the lower goal limit 348 of 8 mmHg, and being greater than the lower normal limit 342 of −10 mmHg. In response to the ICP average being within the goal range, a goal indicator was triggered, thereby causing the minority portion 380 of the background for the ICP textual display 314 from a first color, e.g., black, in FIG. 3 to be a second color, e.g., green, in FIG. 10. In an exemplary embodiment, a color indicating a goal indicator can be different than and be highly contrasting with the color indicating an alarm, e.g., green for a goal indicator and red for an alarm. As discussed above regarding the normal range alarm, the minority and majority portions of the screen 300 can vary. The goal indicator 380 is within the ICP textual display 314, e.g., within the in-goal-range parameter's textual display, in the illustrated embodiment, but the goal indicator 380 can be adjacent the in-goal-range parameter's textual display, within the in-goal-range parameter's graphical display, and/or adjacent the in-goal-range parameter's graphical display.

Although only one goal indicator is shown in FIG. 10, any one or more of the parameters on the screen 300 can, in any combination thereof, have goal indicators therefor. In general, the higher a number of goal indicators present on the screen 300, the more likely that the patient is overall in a relatively good condition, and the lower the number of goal indicators present on the screen 300, the less likely that the patient is overall in a relatively good condition. The number of goal indicators present on the screen 300 can thus be configured as an indicator of the patient's overall condition. A user, e.g., a medical practitioner, etc., observing the screen 300 can thus use the number of goal indicators present on the screen 300 in determining whether to assess and/or treat the patient. In other words, even without seeing or otherwise determining numerical values of any the patient's physiological parameters, the user can determine whether to assess and/or treat the patient, which can facilitate quick decision-making, help reduce errors in reading numbers from the screen 300, help reduce errors in comparing current numerical values to predetermined range(s), and/or facilitate quick patient care. Because color is generally easily discernable even from a relatively large distance, as discussed above, the goal indicator(s) for the physiological parameter(s) on the screen 300 can facilitate assessment of the patient's overall condition without a medical practitioner or other user even having to go into a patient's room and/or get close to the patient.

Figure 11:
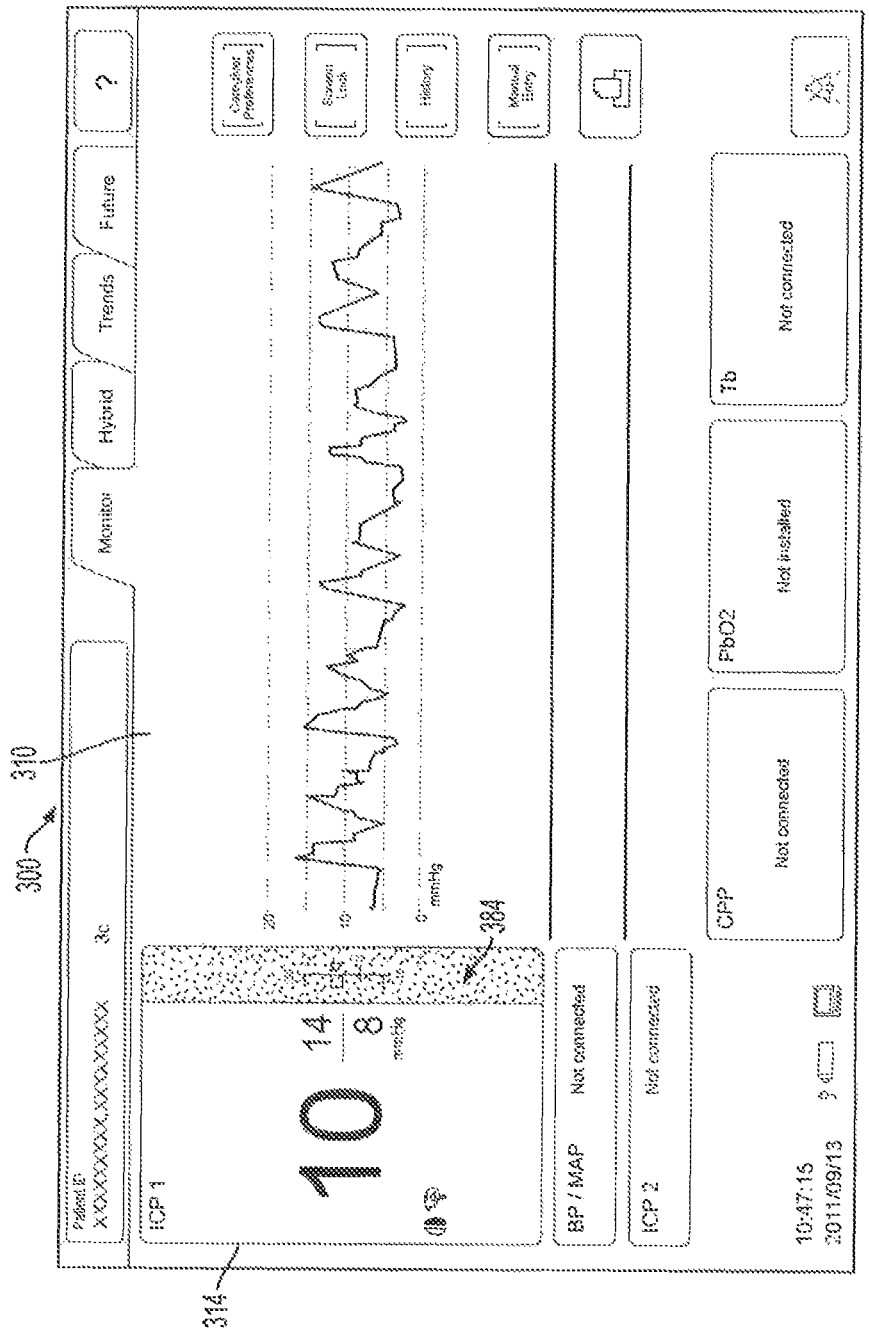
FIG. 11 shows the monitor window of FIG. 5 including a goal indicator for the subset of the physiological parameters.

FIG. 11 shows another embodiment of the display screen 300 when the average ICP is within its predetermined goal range, which in the illustrated embodiment is as discussed above with respect to FIG. 10. FIG. 11 shows the goal indicator being triggered from the monitor window 310 of FIG. 5 in which data is being received for a single physiological parameter, ICP. The goal indicator in FIG. 11 includes, similar to FIG. 10, a minority portion 384 of the background color of the ICP textual display 314 changing colors (black to green).

Figure 12:
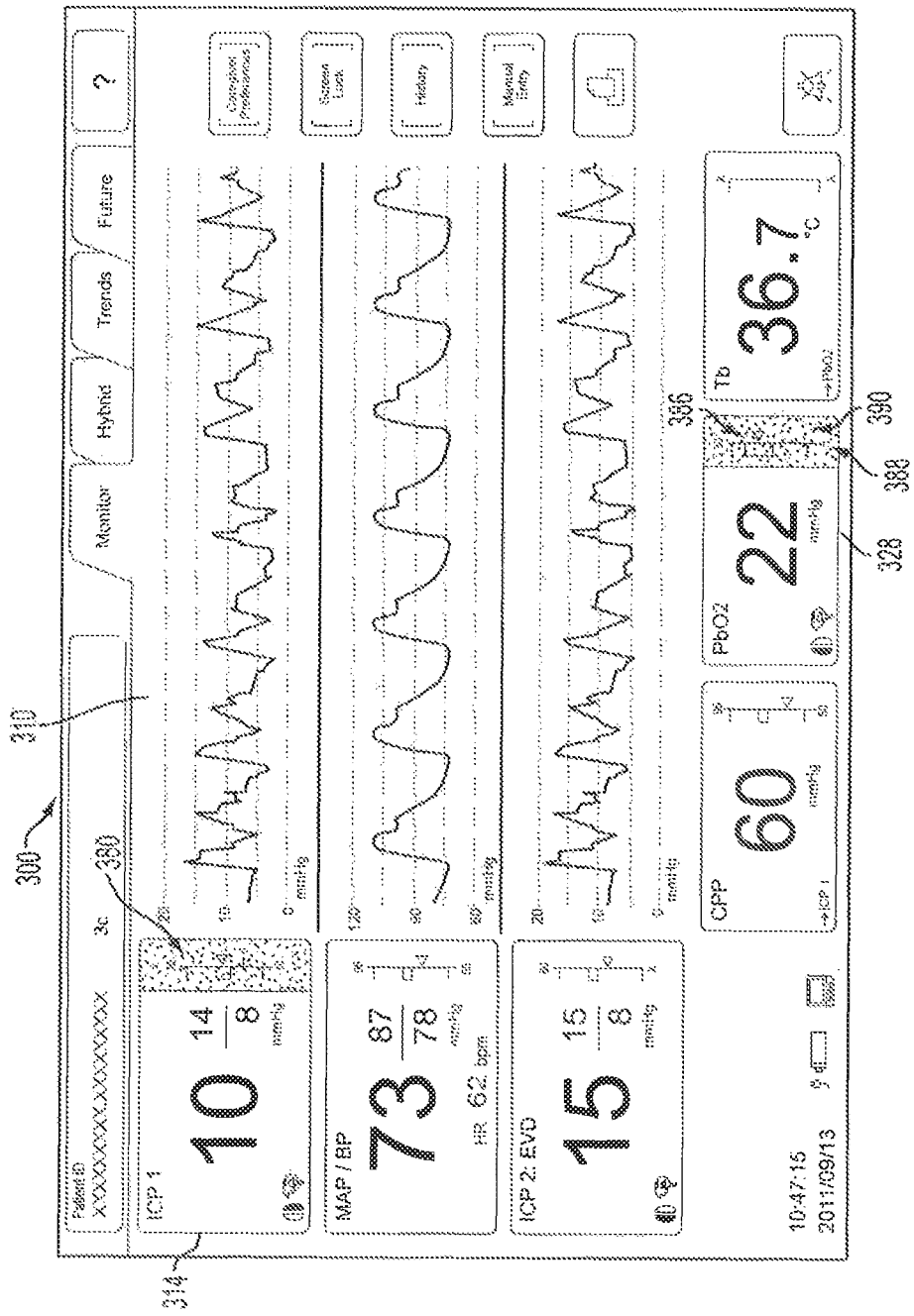
FIG. 12 shows the monitor window of FIG. 10 including a goal indicator for an oxygen saturation one of the physiological parameters.

FIG. 12 shows an embodiment of the display screen 300 when the averages of a plurality of physiological parameters are within their respective goal ranges. In the illustrated embodiment, ICP is within its predetermined goal range as discussed above with respect to FIG. 10, and PbO2 is within its predetermined goal range, which in the illustrated embodiment is the PbO2 average of 22 mmHg being less than an upper goal limit of 23 mmHg, being less than an upper normal limit 386 of 30 mmHg, being greater than a lower goal limit of 17 mmHg, and being greater than a lower normal limit 388 of 0 mmHg. FIG. 12 shows the goal indicators for ICP and PbO2 being triggered from the monitor window 310 of FIG. 3. The goal indicators in FIG. 12 includes, similar to FIG. 11, a minority portion 384 of the background color of the ICP textual display 314 changing colors (black to green) and a minority portion 390 of the background color of the PbO2 textual display 328 changing colors (black to green). In the illustrated embodiment, the EVD ICP, CPP, and Tb physiological parameters are outside their respective goal ranges and within their respective normal ranges such that alarms and goal indicators are not shown for any of the EVD ICP, CPP, and Tb.

Figure 13:
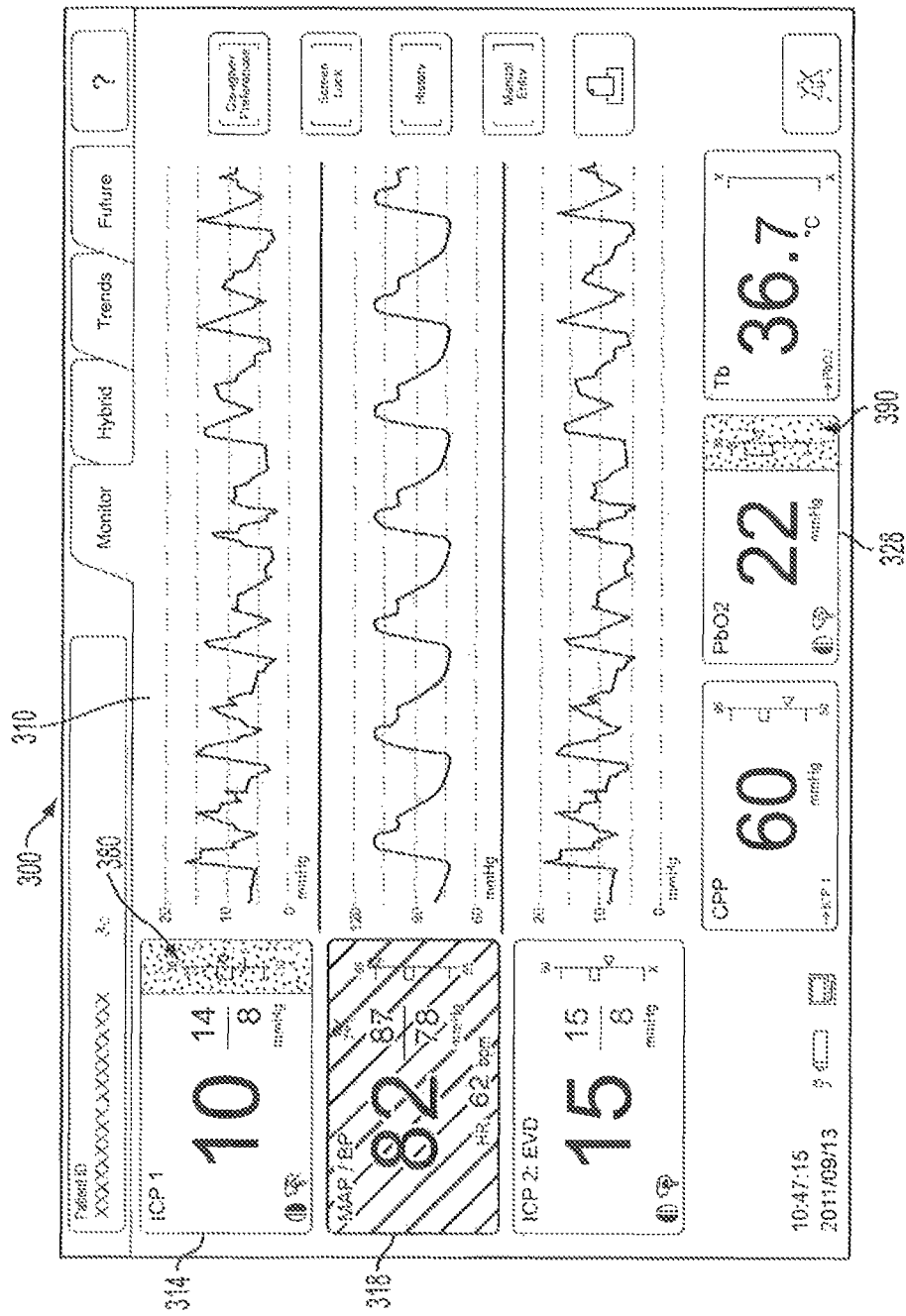
FIG. 13 is a shows the monitor window of FIG. 12 including an alarm for a mean arterial pressure/blood pressure and heart rate ones of the physiological parameters.

FIG. 13 shows an embodiment of the display screen 300 when at least one of the physiological parameters is within its respective goal range and when at least one other of the physiological parameters is outside its respective normal range. In the illustrated embodiment, the ICP and PbO2 physiological parameters are within their respective goal ranges as discussed above regarding FIG. 12, the EVD ICP, CPP, and Tb physiological parameters are outside their respective goal ranges and within their respective normal ranges as discussed above regarding FIG. 12, and the MAP/BP physiological parameter is outside its normal range, e.g., by being below its predetermined lower limit for its normal range. The MAP/BP alarm is shown in FIG. 13 as having been acknowledged similar to that discussed above regarding the acknowledgement of the ICP alarm of FIG. 9. Although only two goal indicators and only one alarm are shown in FIG. 13, any combination of any of the parameters on the screen 300 can have goal indicators or alarms therefor.

A duration of the goal state can be determined and stored, e.g., in a storage unit, which can facilitate evaluation of the patient's condition, e.g., if displayed on the screen 300. In other words, start and stop times of the goal indicator's presence on the screen 300 can be saved.

When a goal indicator is triggered for a physiological parameter, the goal indicator can persist until the parameter falls outside its associated goal range. The goal indicator can thus be configured to continuously indicate in-goal-range status of its associated physiological parameter. In an exemplary embodiment, the goal indicator can be configured to be non-removable, e.g., user input cannot cause the goal indicator to be removed from the screen 300. In other words, a goal indicator can be configured to always be present on the screen 300 for its associated physiological parameter unless the parameter is out of goal range. In this way, the screen 300 can be configured to always provide an indication of each parameter's goal range status. The screen 300 can thus be configured to continuously provide goal range status information in a consistent way, e.g., with a textual display's minority portion remaining a same color if within the goal range and remaining same color if outside the goal range, thereby facilitating unambiguous assessment of parameters' goal range statuses. The goal indicator can, however, be configured to be removed from and/or altered on the screen 300, such as by being acknowledged similar to that discussed above regarding acknowledgement of the alarm. The screen 300 can thus include a goal indicator acknowledgement button (not shown) similar to the alarm silence button 374.

As discussed above, a goal indicator can be triggered for a physiological parameter, e.g., ICP, MAP/BP, HR, EVD ICP, CPP, PbO2, and Tb, in response to its average being within its predetermined goal range. Additionally or alternatively, a goal indicator can be triggered for a physiological parameter in response to a pattern of individual values for the physiological parameter gathered from the patient being consistent with a predetermined pattern of values for the physiological parameter. In other words, a goal alarm can be triggered in response to a pattern of individual values varying from a predetermined pattern of values. As discussed above, triggering the goal alarm can cause the goal indicator for that physiological parameter to be removed from the screen 300, if the goal indicator for that physiological parameter was already present thereon, or cause the goal indicator for that physiological parameter to remain off the screen 300, if the goal indicator for that physiological parameter was already not present thereon. The goal indicator can thus be configured to not be present on the screen 300 in some circumstances for a parameter even when the parameter's current value is within that parameter's goal range. In this way, the goal indicator can be configured to indicate whether or not the physiological parameter is trending to be outside its associated goal range and/or outside its associated normal range. The patient's condition can thus be assessed and/or treated before the patient's condition further deteriorates, e.g., before the physiological parameter's average has a chance to be outside the normal range and/or outside the goal range. The predetermined pattern of values can include a variety of different patterns.

In an exemplary embodiment, the predetermined pattern can include a predetermined number of immediately successive gathered or calculated values each increasing from its immediately preceding gathered or calculated value. In other words, if a predetermined number of values successively increase, e.g., indicating an upward trend, the goal alarm can be triggered for that parameter. The predetermined number can be any number two or greater, and in an exemplary embodiment is at least ten, e.g., such that the eleventh increased value in a row can trigger the goal alarm. The predetermined number can vary between different parameters, e.g., a higher predetermined number for physiological parameters that are gathered more frequently than other physiological parameters.

In another exemplary embodiment, the predetermined pattern can include a predetermined number of immediately successive gathered or calculated values each decreasing from its immediately preceding gathered or calculated value. In other words, if a predetermined number of values successively decrease, e.g., indicating a downward trend, the goal alarm can be triggered for that parameter. The predetermined number can be any number two or greater, and in an exemplary embodiment is at least ten, e.g., such that the eleventh decreased value in a row can trigger the goal alarm. The predetermined number can vary between physiological parameters, e.g., a higher predetermined number for physiological parameters that are gathered more frequently than other physiological parameters.

In yet another exemplary embodiment, the predetermined pattern can include a gathered or calculated value being a predetermined threshold amount greater than its immediately preceding value. In other words, the predetermined trend can include a sudden spike up in value. The predetermined threshold amount can vary between different parameters, e.g., a higher predetermined threshold amount for physiological parameters that are gathered more frequently than other physiological parameters.

In another exemplary embodiment, the predetermined pattern can include a gathered or calculated value being a predetermined threshold amount less than its immediately preceding value. In other words, the predetermined trend can include a sudden spike down in value. The predetermined threshold amount can vary between different parameters, e.g., a lower predetermined threshold amount for physiological parameters that are gathered less frequently than other physiological parameters.

In another exemplary embodiment, the predetermined pattern can include a gathered or calculated value being a predetermined threshold amount greater than the current average value for that parameter. In other words, the predetermined pattern can include a sudden spike up in value. The predetermined threshold amount can vary between different parameters, e.g., a higher predetermined threshold amount for physiological parameters that are gathered more frequently than other physiological parameters.

In another exemplary embodiment, the predetermined pattern can include a gathered or calculated value being a predetermined threshold amount less than the current average value for the parameter. In other words, the predetermined pattern can include a sudden spike down in value. The predetermined threshold amount can vary between different parameters, e.g., a lower predetermined threshold amount for physiological parameters that are gathered less frequently than other physiological parameters.

In another exemplary embodiment, the predetermined pattern can include one or more of the physiological parameters meeting a predetermined condition, thereby triggering a goal alarm for a different one or more of the physiological parameters. In other words, one or more of the physiological parameters can be cross-correlated with one or more others of the physiological parameters such that values of the one or more of the physiological parameters can affect the one or more others of the physiological parameters. For example, CPP can be cross-correlated with ICP and MAP such that if one or both of ICP and MAP fall outside their respective goal ranges and/or fall outside their respective normal ranges, a goal alarm can be triggered for CPP, e.g., a goal indicator for CPP can be removed from the screen 300 if not already absent from the screen 300. In other words, the predetermined condition can be, for example, ICP and/or MAP falling outside their respective goal ranges and/or fall outside their respective normal ranges. For another example, MAP/BP can be cross-correlated with ICP such that if one of ICP and MAP/BP is increasing, e.g., its average is increasing, and the other one of ICP and MAP/BP is decreasing, e.g., its average is decreasing, a goal alarm can be triggered for both ICP and MAP/BP. In other words, the predetermined condition can be, for example, one of ICP and MAP/BP increasing and the other one of ICP and MAP/BP decreasing. ICP and MAP/BP both relate to pressure, so if one of ICP and MAP/BP is increasing while the other of ICP and MAP/BP is decreasing over the same current time period, the patient may be in distress even if ICP and MAP/BP are both within their goal ranges. For another example, MAP/BP can be cross-correlated with ICP such that if ICP is increasing or decreasing opposite from MAP/BP, e.g., ICP's average is increasing and MAP/BP's average is decreasing, or ICP's average is decreasing and MAP/BP's average is increasing, a goal alarm can be triggered for ICP. In other words, the predetermined condition can be, for example, ICP's average trending opposite to that of MAP/BP's average.

Predetermined numbers, predetermined threshold amounts, and predetermined conditions for predetermined patterns can each, same or different from one another, be a default, preprogrammed value, e.g., preprogrammed into a processor, or can be customized for a particular patient.

The device can be configured to consider any number of predetermined patterns. In other words, any number of predetermined patterns can be preprogrammed into the device such that the goal alarm can be configured to be triggered based on any one or more predetermined patterns and/or based on the goal range. In some embodiments, alarms related to the predetermined normal ranges for physiological parameters can be based on predetermined patterns similar to that discussed above regarding predetermined goal ranges.

As mentioned above, selection of the hybrid tab 304 on the display screen 300 can cause a hybrid window to be shown on the screen 300. The hybrid window can be configured to show information for one or more physiological parameters over a current time period and can show information for the one or more physiological parameters over another time period, also referred to herein as a "trend time period," that is different from the current time period. The hybrid window can thus facilitate comparison of current information with previously gathered information, which can facilitate a more long term analysis of the patient's physiological parameters. The information for the one or more physiological parameters over the current time period can include information similar to that discussed above regarding the information that can be shown on the monitor window. The information for the one or more physiological parameters over the other time period can include information that can be shown on the trends window. The hybrid window can thus be configured as a hybrid of the monitor window and the trends window. The information displayed in the hybrid window for each of the physiological parameters can be based on data received by the monitoring device in any of a variety of ways, as discussed above. For each of the physiological parameters shown on the screen, the hybrid window can be configured to show at least one of a textual display of parameter information for the current time period and a graphical display of parameter information for the current time period, and at least one of a textual display of parameter information for a trend time period and a graphical display of parameter information for the trend time period.

In an exemplary embodiment, the trend time period can be longer than the current time period, e.g., fifteen minutes, thirty minutes, ninety minutes, one hundred minutes, etc., although virtually any time period can be used as the trend time period. In some embodiments, the trend time period can be hours, days, or longer, and can be adjustable as discussed above with respect to the current time period. The trend time period can entirely precede the current time period or can overlap at least partially with the current time period. In some embodiments, the trend time period can correspond to requirements of a particular physiological parameter. For example, the trend time period can correspond to a time period pertinent to ICP monitoring and thereby allow a caregiver to review this trend time period. Various embodiments of displaying trends for a physiological parameter on a display screen are described in further detail in U.S. Pat. Pub. No. 2009/0005703.

Figure 14:
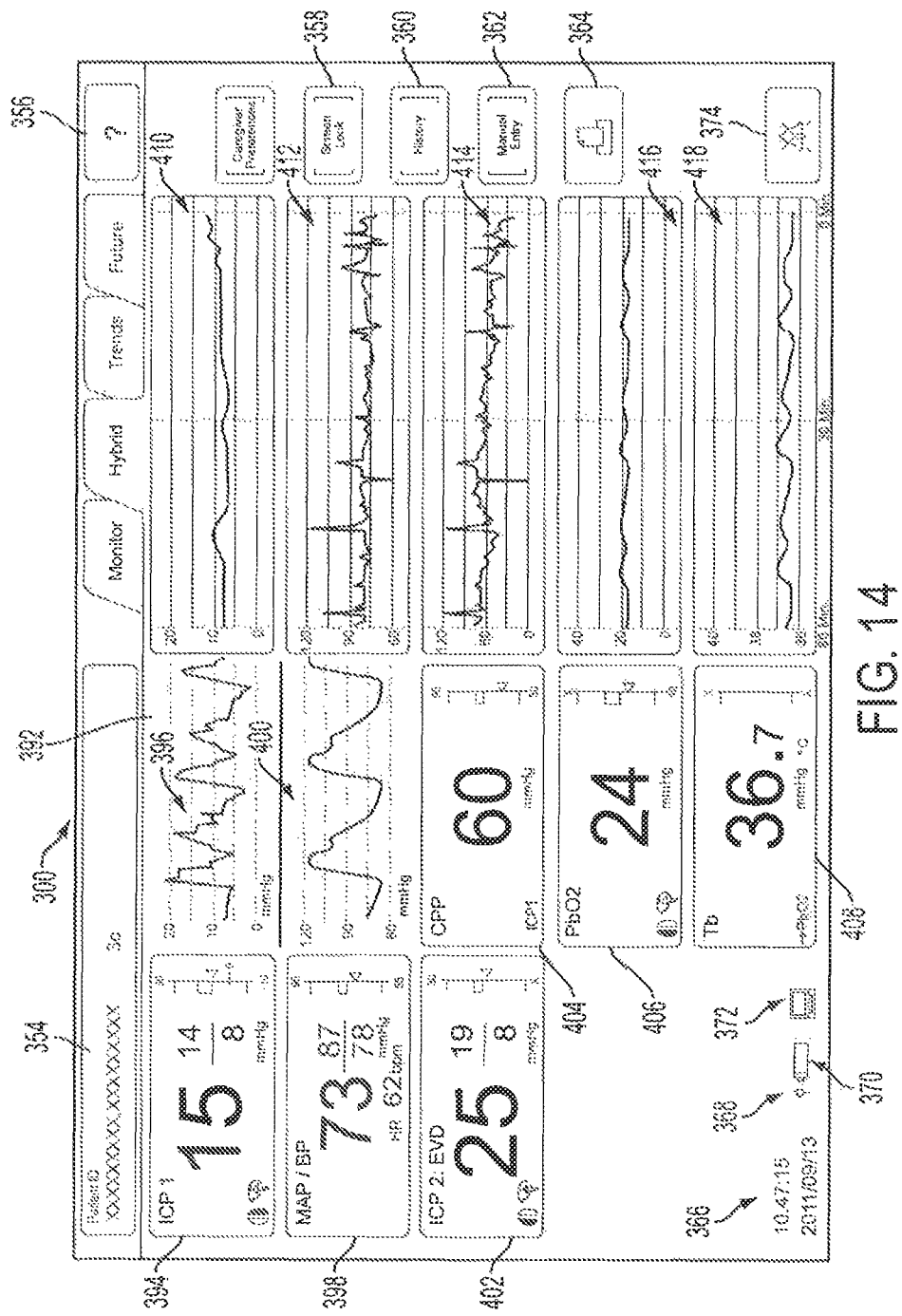
FIG. 14 is an embodiment of a hybrid window of the medical monitoring system of FIG. 3, the hybrid window showing current information for a plurality of physiological parameters and trends information for a subset of the physiological parameters.

FIG. 14 shows an embodiment of a hybrid window 392 on the display screen 300. As mentioned above, the hybrid window 392 can include one or more static features, such as the patient ID window 354, the help button 356, the screen lock button 358, the history button 360, the manual entry button 362, the print button 364, the current date/time indicator 366, the power connector 368, the charge indicator 370, the docking indicator 372, and the alarm silence button 374. In the illustrated embodiment, the hybrid window 392 shows information over the current time period for ICP in an ICP textual display 394 and an ICP graphical display 396, MAP/BP in a MAP/BP textual display 398 and a MAP/BP graphical display 400, HR in the MAP/BP textual display 398, EVD ICP in an EVD textual display 402, CPP in a CPP textual display 404, PbO2 in a PbO2 textual display 406, and Tb in a Tb textual display 408, but as mentioned above, any one or more physiological parameters can be monitored and displayed, and current information for any one or more physiological parameters can be shown on the hybrid window 392 in textual displays and/or graphical displays. In the illustrated embodiment, the hybrid window 392 shows information over the trend time period for ICP in an ICP trends window 410, for MAP/BP in a MAP/BP trends window 412, for CPP in a CPP trends window 414, for PbO2 in a PbO2 trends window 416, and for Tb in a Tb trends window 418, but any one or more physiological parameters can be monitored and displayed, and trends information for any one or more physiological parameters can be shown on the hybrid window 392 in textual displays and/or graphical displays similar to the textual displays and graphical displays discussed above regarding the monitor window. Which one or more of the physiological parameters have a textual display only, have a graphical display only, or have both a textual display and a graphical display can be user-adjusted, such as by dragging and dropping displays on the touchscreen or activating the preferences button 312.

As shown in the embodiment of FIG. 14, the hybrid window 392 can display a trendline in each of the ICP trends window 410, the MAP/BP trends window 412, the CPP trends window 414, the PbO2 trends window 416, and the Tb trends window 418 as related to each of their respective physiological parameters. The trendline for each of the physiological parameters can represent its associated physiological parameter graphically via a graph line, however virtually any graphical representation can be used, such as a bar graph, a plot of discrete data points, and/or other pictorial display. Each of the ICP trends window 410, the MAP/BP trends window 412, the CPP trends window 414, the PbO2 trends window 416, and the Tb trends window 418 in the illustrated embodiment plots via the trendline their respective physiological parameter's values gathered and/or calculated during the trend time period. However, a trends window can show (e.g., via a graph line and/or other pictorial display) values of another statistic based on its associated physiological parameter, e.g., a mean value of the physiological parameter calculated over a sample period, e.g., every two to three seconds, a median value, a normalized value, a systolic value, a diastolic value, wave amplitude, etc.

Figure 15:
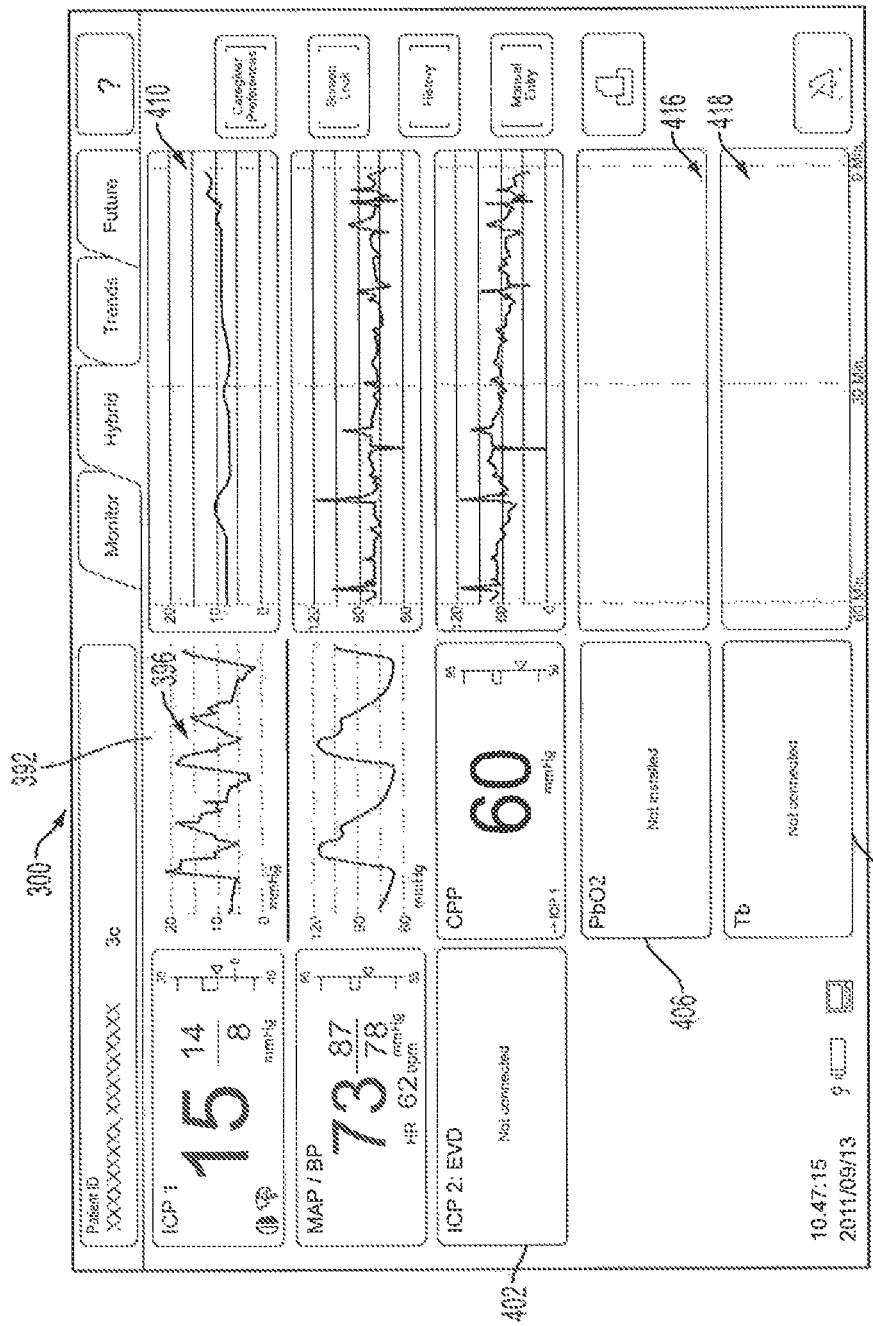
FIG. 15 shows the hybrid window of FIG. 14 including current information for another subset of the physiological parameters.

In some instances, data may not be received for a certain physiological parameter, as mentioned above, such that those missing physiological parameter(s) can be absent from the hybrid window 392. FIG. 15 shows an example of the hybrid window 392 in which data is being received for a plurality of physiological parameters, e.g., ICP, MAP/BP and HR, and CPP, and is not being received for a plurality of physiological parameters, e.g., EVD ICP, PbO2, and Tb. The hybrid window 392 in this illustrated embodiment thus lacks graphical displays for EVD ICP, PbO2, and Tb over the current time period, lacks textual displays for EVD ICP, PbO2, and Tb over the trend time period, lacks graphical displays for EVD ICP, PbO2, and Tb over the trend time period in the PbO2 graphical display 416 and in the Tb graphical display 418, and lacks any numerical data in the textual displays 402, 406, 408 for EVD ICP, PbO2, and Tb. In the illustrated embodiment, the textual displays 402, 406, 408 for EVD ICP, PbO2, and Tb each include a data absence indicator in the form of a textual message, "Not connected" in the EVD ICP and Tb displays 402, 408 and "Not installed" in the PbO2 display 406.

Similar to that discussed above regarding the monitor window 310, the textual display(s) and/or the graphical display(s) for each of the physiological parameters ICP, MAP/BP and HR, EVD ICP, CPP, PbO2, and Tb shown on the hybrid window 392 can be configured to be observed by a user so as to assess the patient's condition. To facilitate assessment of the patient's condition, an alarm can be provided if any of the physiological parameters fall outside their associated normal range, also similar to that discussed above regarding the monitor window 310. In an exemplary embodiment, when an alarm for a physiological parameter is triggered, the monitor portion of the hybrid window 392 for that physiological parameter can be configured to indicate the alarm, while the trends portion of the hybrid window 392 for that physiological parameter can be configured to not change in response to the alarm condition, e.g., not change color, not include an alarm symbol thereon, etc. Not changing the trends portion of the hybrid window 392 in response to the alarm condition can reflect that current conditions are in an alarm state rather than indicate that an error exists in the longer-term trend of the physiological parameter reflected in any trends display in the hybrid window 392 for that physiological parameter. The trends portion of the hybrid window 392 for that physiological parameter can, however, be configured to change in response to the alarm similar to that discussed above regarding the monitor window.

Figure 16:
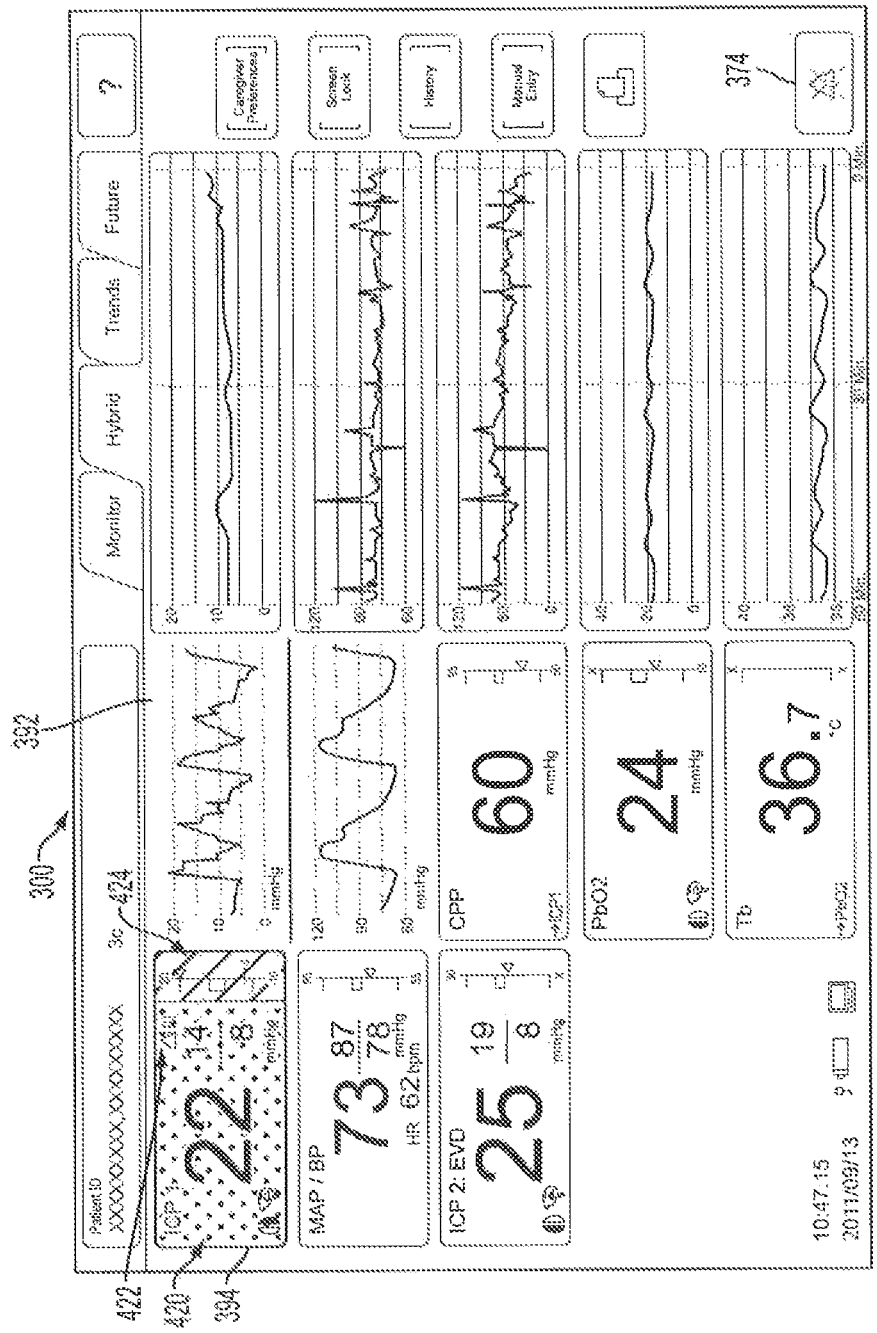
FIG. 16 shows the hybrid window of FIG. 14 including an alarm for an ICP one of the physiological parameters.

FIG. 16 shows an embodiment of the display screen 300 after the average ICP falls outside its predetermined normal range, which in the illustrated embodiment is the average exceeding the upper normal limit, e.g., the current average value of 22 mmHg being above the upper normal limit of 20 mmHg. In response to the ICP average falling outside the normal range, an alarm was triggered, thereby changing a majority portion 420 of the background for the ICP textual display 394 from a first color, e.g., black, in FIG. 14 to a second color, e.g., red, in FIG. 16, and thereby causing an alarm symbol 422 to be shown in the ICP textual display 394. Although only one alarm is shown in FIG. 16, any one or more of the parameters on the screen 300 can, in any combination thereof, have alarms therefor. The embodiment shown in FIG. 16 does not alter the ICP graphical display 396 or the ICP trends portion of the hybrid window 392, e.g., the ICP trends window 410, in response to the detected alarm condition for ICP.

Figure 17:
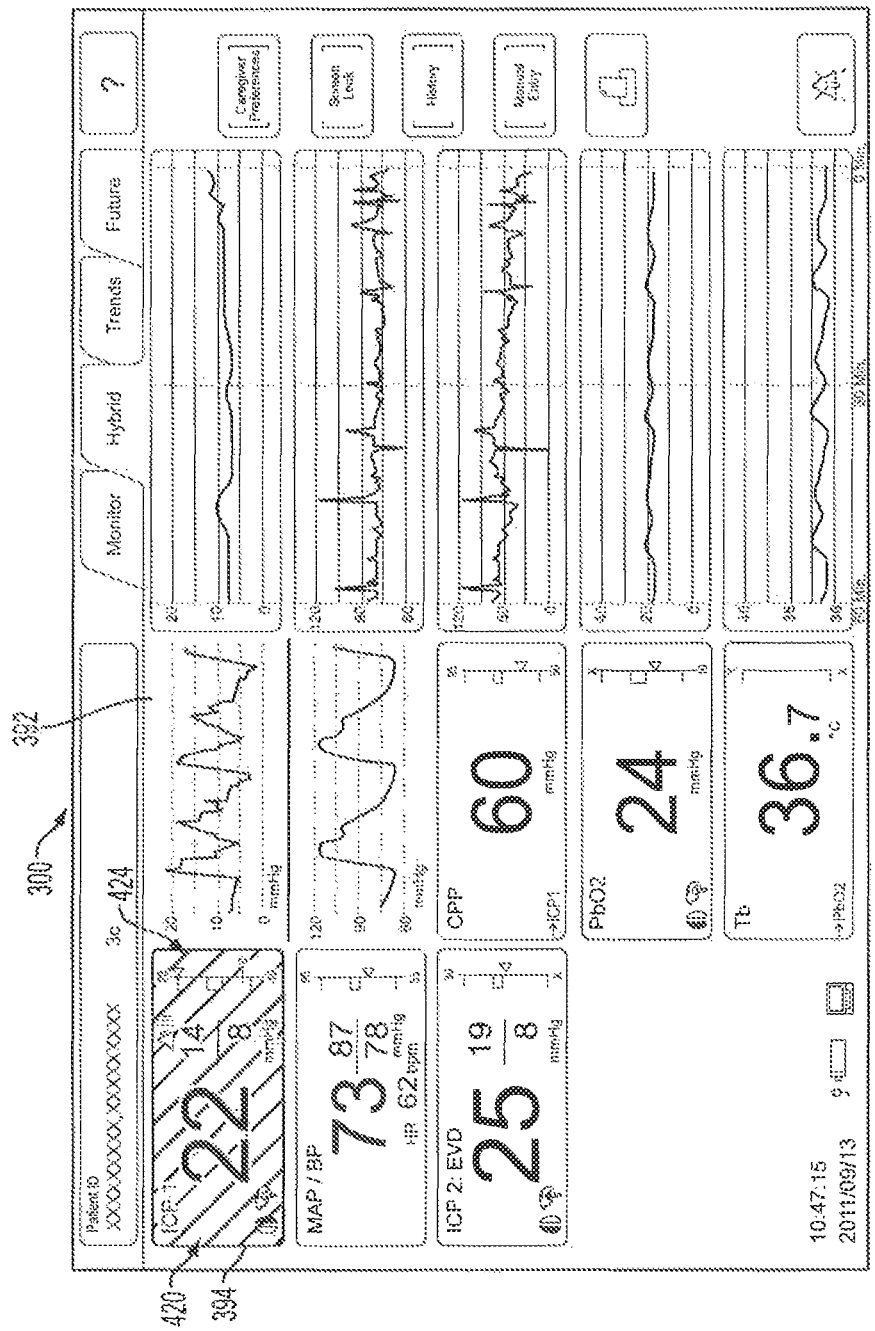
FIG. 17 shows the hybrid window of FIG. 16 including an alarm acknowledgement for the ICP one of the physiological parameters.

An alarm on the hybrid window 392 can be acknowledged similar to that discussed above regarding the monitor window. FIG. 17 shows an embodiment of the display screen 300 after acknowledgement of the alarm of FIG. 16. In response to the alarm being acknowledged, e.g., in response to activation of the alarm silence button 374, an acknowledgement was triggered, thereby changing the majority portion 420 of the background for the ICP textual display 394 from the second color, e.g., red, in FIG. 16 to a third color, e.g., white, in FIG. 16. A minority portion 424 of the background for the ICP textual display 394 did not change from FIG. 16 to FIG. 17. The alarm symbol 422 can remain present on the display screen 300 even after the alarm has been acknowledged, as shown in FIG. 17.

Figure 18:
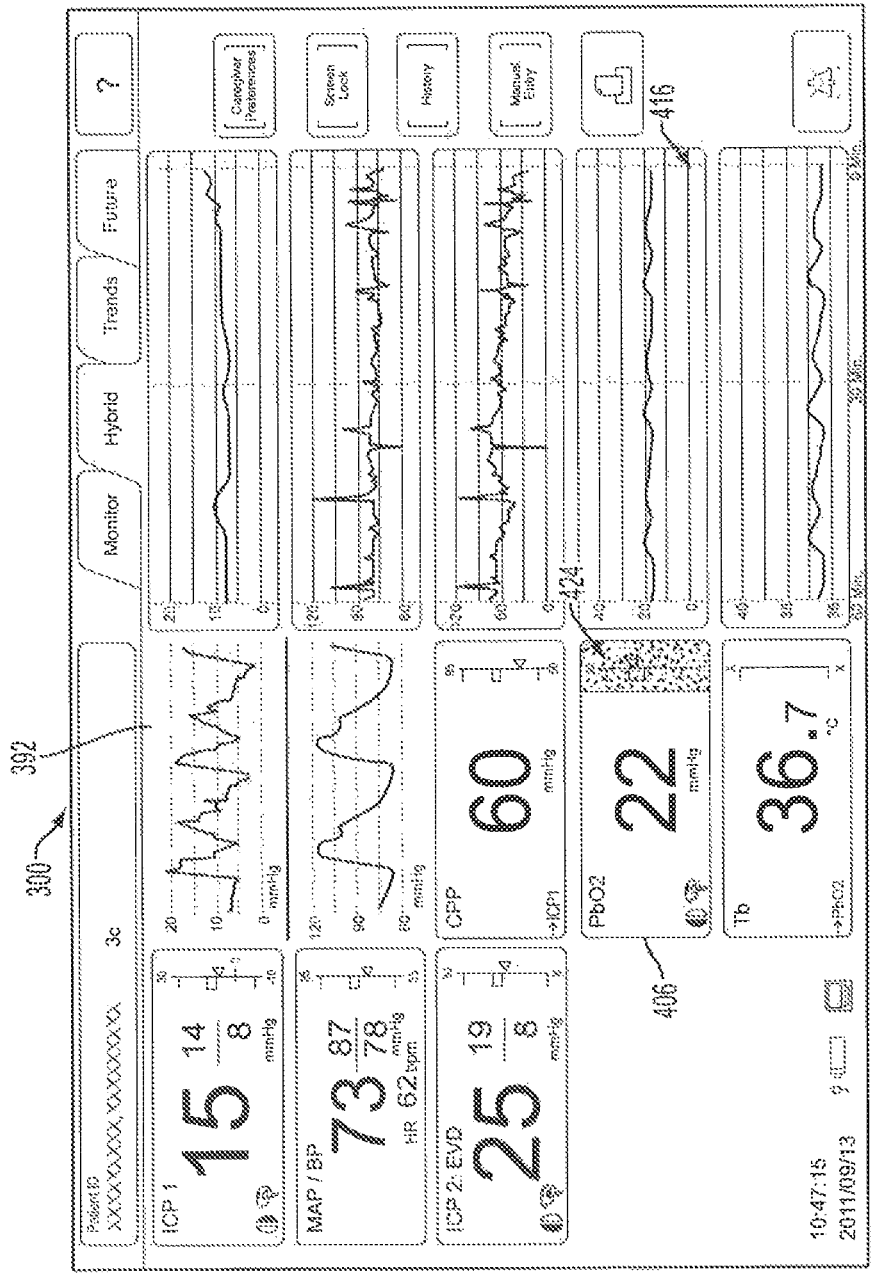
FIG. 18 shows the hybrid window of FIG. 14 including a goal indicator for an oxygen saturation one of the physiological parameters.
Figure 19:
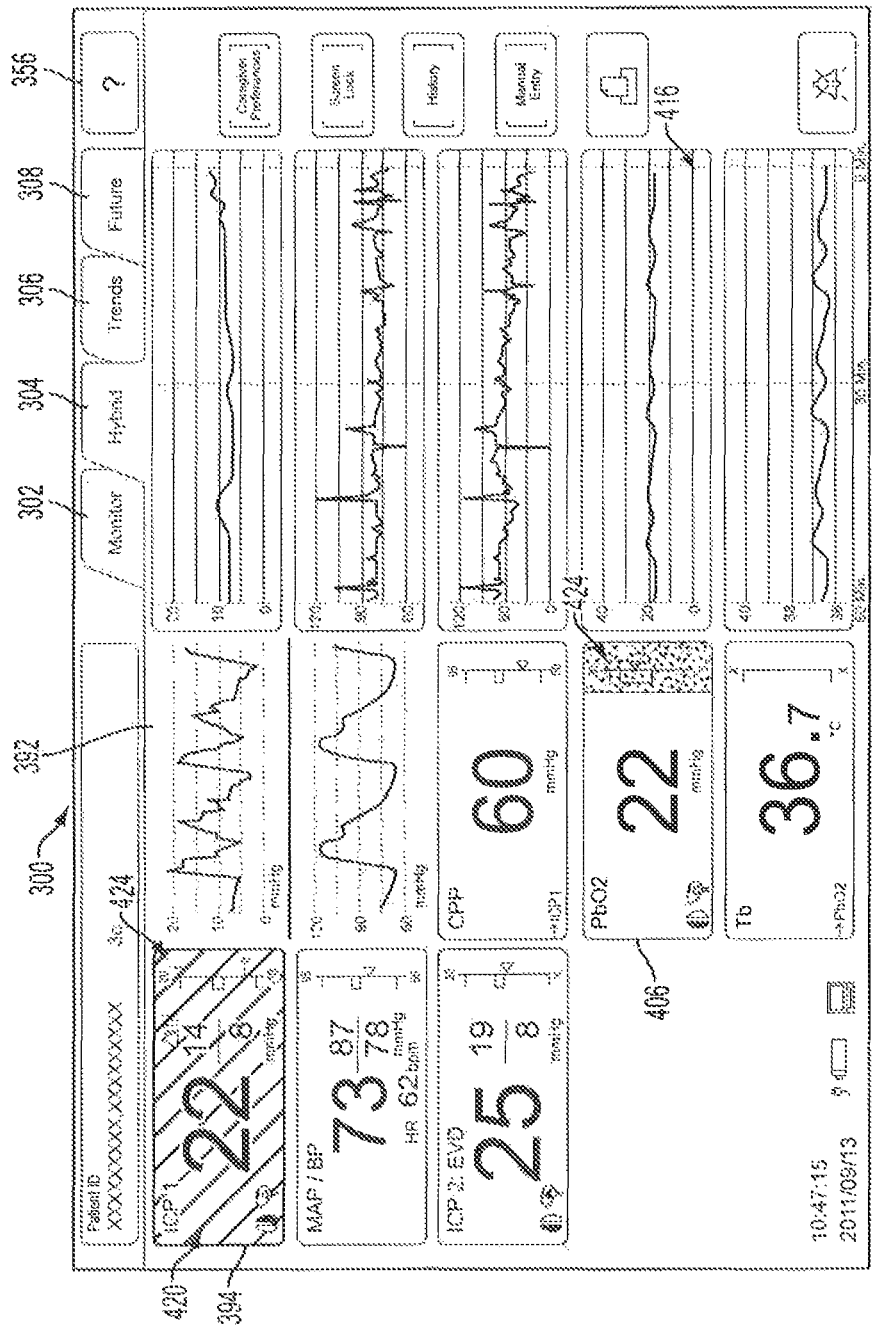
FIG. 19 shows the hybrid window of FIG. 17 including a goal indicator for an oxygen saturation one of the physiological parameters.

Also similar to that discussed above regarding the monitor window, a goal alarm can be provided on the hybrid window 392 based on any one or more factors, e.g., if any of the physiological parameters are outside their associated goal range and/or any of the physiological parameters deviate from one or more predetermined trends. FIG. 18 shows an embodiment of the hybrid window 392 of FIG. 14 after the average PbO2 has changed to be within its predetermined goal range. In response to the PbO2 average being within the goal range, a goal indicator was triggered, thereby changing a minority portion 424 of the background for the PbO2 textual display 406 from a first color, e.g., black, in FIG. 14 to a second color, e.g., green, in FIG. 18. The embodiment shown in FIG. 18 does not alter the PbO2 trends portion of the hybrid window 392, e.g., the PbO2 trends window 416, in response to the detected goal condition for PbO2. FIG. 19 shows an embodiment of the hybrid window 392 of FIG. 14 when at least one of the physiological parameters has changed within its respective goal range, e.g., PbO2 similar to that discussed above regarding FIG. 18, and when at least one other of the physiological parameters is outside its respective normal range and has been acknowledged as being so, e.g., ICP similar to that discussed above regarding FIG. 17.

Figure 20:
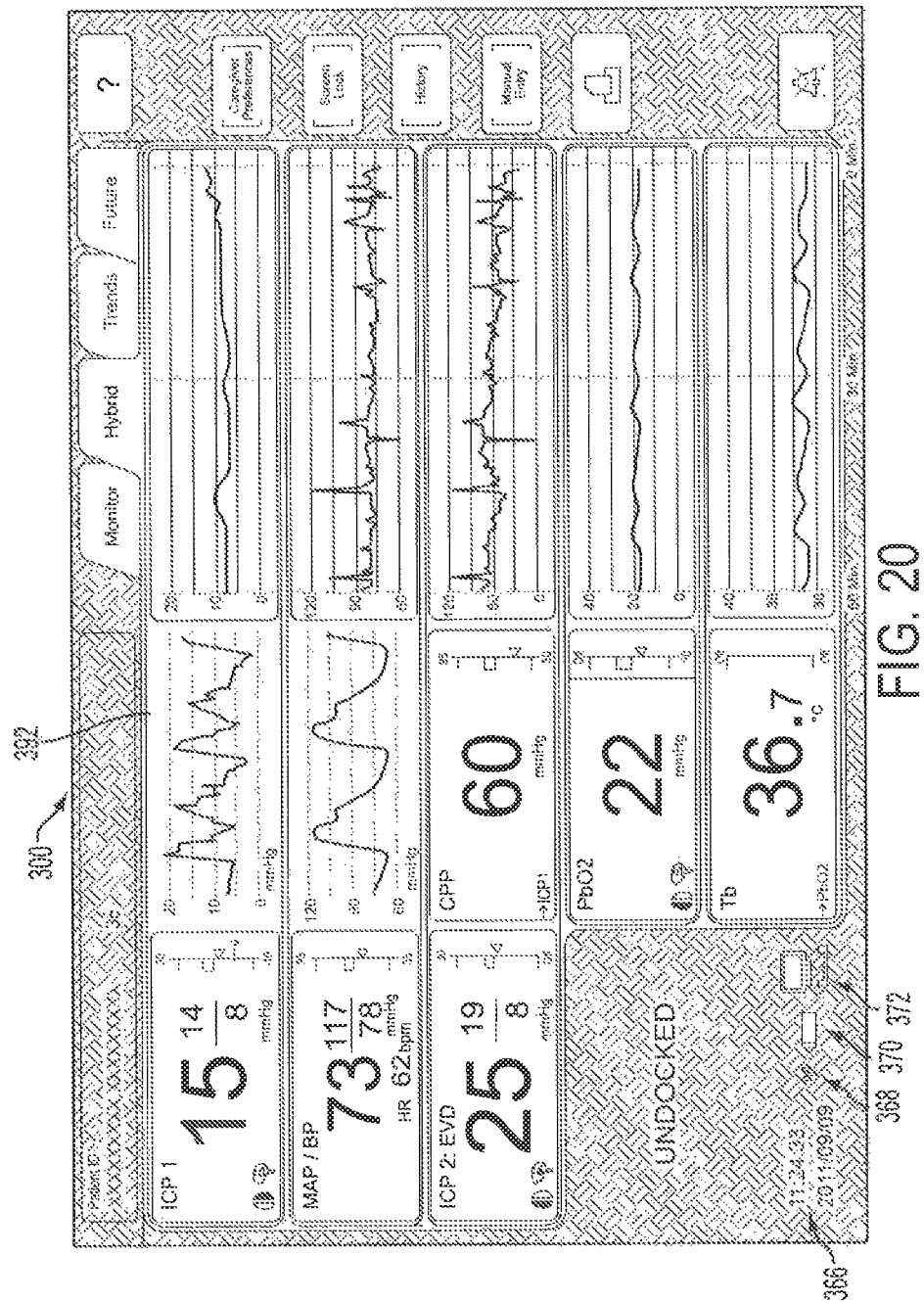
FIG. 20 shows the hybrid window of FIG. 18 when the medical monitoring system is undocked.
Figure 21:
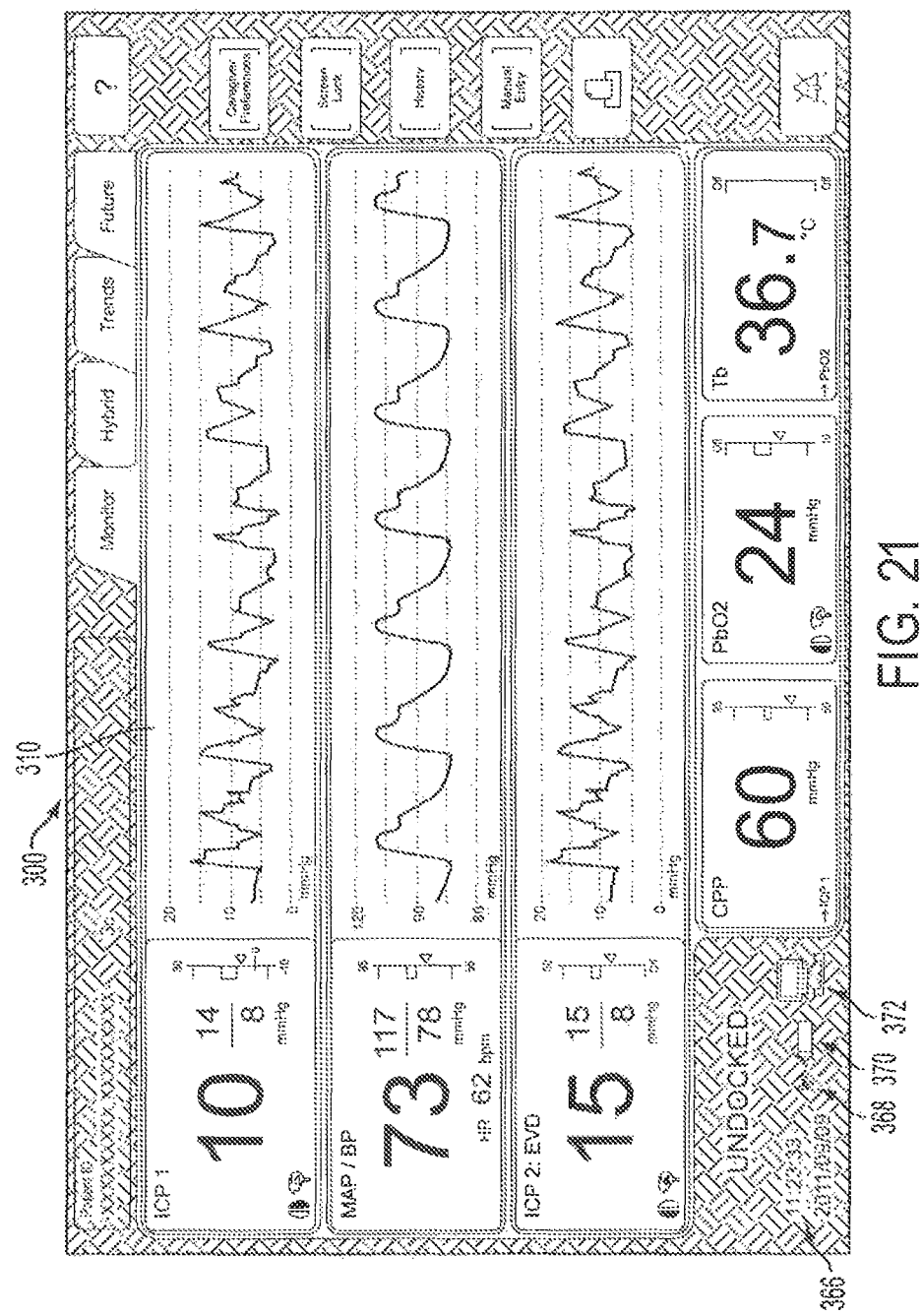
FIG. 21 shows the monitor window of FIG. 3 when the medical monitoring system is undocked.

FIG. 20 shows an embodiment of the hybrid window 392 of FIG. 18 when the device is undocked, e.g., is running from an on-board power supply such as a battery. The undocked state of the device can be indicated in any one or more ways, such as by changing a background color of the display screen 300 (e.g., from white in FIG. 18 to yellow in FIG. 20, changing the docking indicator 372 (e.g., from a docked icon in FIG. 18 to an undocked icon in FIG. 20), a textual identifier (e.g., "UNDOCKED" on the screen 300 in FIG. 20), etc. Providing clear notice of the device being undocked can help prevent the device from running out of power, going out of range, etc. FIG. 21 similarly shows an embodiment of the monitor window 310 of FIG. 3 when the device is undocked.

As mentioned above, the relative sizes and locations of the various windows, symbols, text, icons, etc. shown for the hybrid window 392 of FIGS. 14-20 and the monitor window 310 of FIG. 21 are exemplary in nature.

As mentioned above, selection of the trends tab 306 on the display screen 300 can cause a trends window (not shown) to be displayed on the screen 300. The trends window can include information similar to the trends information that can be shown in the hybrid window, as discussed above. As also mentioned above, various embodiments of providing trends information are discussed further in U.S. Pat. Pub. No. 2009/0005703.

As mentioned above, selection of the future tab 308 on the display screen 300 can cause a future window (not shown) to be displayed on the screen 300. The future window can show information for one or more physiological parameters in a future time period that is after the current time period. The future time period can be a predetermined amount of time that can be a default, preprogrammed time period, e.g., preprogrammed into a processor, or can be customized for a particular patient. The future time period can be, e.g., in a range of about five to sixty seconds, in a range of about five to ten seconds, a single heartbeat, a most recent few heartbeats of the patient, etc. The future time period can be adjustable similar to that discussed above, such as when a user activates the preferences menu or soft button 312. Adjustment of the future time period can allow for various clinical protocols, as such protocols can require tracking of a parameter over different time periods.

Any one or more physiological parameters can be shown on the future window. The information displayed for each of the physiological parameters can be based on data received by the monitoring device in any of a variety of ways, as discussed above. For each of the physiological parameters, the future window can be configured to show a textual display of parameter information for the future time period and/or a graphical display of parameter information for the future time period, similar to the textual and graphical displays discussed above. Which one or more of the physiological parameters have a textual display only, have a graphical display only, or have both a textual display and a graphical display can be user-adjusted, such as by dragging and dropping displays on the touchscreen or activating the preferences button 312. The future data can be shown in the future window in any one or more ways, such as by scatter plots, spider plots, plotting one parameter against another, plotting one parameter against another within a specific period of time, 3D plot (where the third axis is time).

The parameter information shown on the future window can be based on analysis of actual parameters values gathered from the patient. In other words, the information for a physiological parameter in the future time period can include projections of future parameter values based on actual values of that parameter gathered from the patient. Future parameter values for a physiological parameter can be extrapolated from the actual values gathered from the patient for that parameter using any one or more extrapolation techniques, as will be appreciated by a person skilled in the art. Examples of extrapolation techniques include linear extrapolation, linear extrapolation, conic extrapolation, and polynomial extrapolation. Various software known in the art can be used to perform such extrapolation, such as Fityk (available under GNU General Public License), Ch (marketed by SoftIntegration, Inc. of Davis, Calif.), ZunZun.com (online curve fitting), and savetman.com (online curve fitting using least squares fit with weights). The future data can be correlated (e.g., autocorrelated and/or cross correlated) and/or the future data can be manipulated for frequency analysis.

FIGS. 3-19 are directed to user interfaces in a neurological context, e.g., for use in monitoring a patient with a traumatic brain injury. However, the methods, systems, and devices described herein are applicable in other medical contexts and can be used in monitoring a patient having virtually any ailment(s). Also, while FIGS. 3-19 use ICP, MAP/BP, HR, EVD ICP, CPP, PbO2, and Tb as exemplary physiological parameters, this is by way of illustration only. The methods, systems, and devices described herein can be applied to virtually any physiological parameters of a patient.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system, comprising:
a display screen; and
a processor configured to:
receive a plurality of values of a physiological parameter measured from a patient over a period of time,
determine if a current value based on the received values is within a normal range of the physiological parameter,
cause an alarm indicator to be displayed on the display screen if the current value is determined to not be within the normal range, the alarm indicator not being displayed on the display screen if the current value is determined to be within the normal range,
determine if the current value is within a goal range of the physiological parameter, the goal range being a subset of the normal range, and
cause a goal indicator to be displayed on the display screen if the current value is determined to be within the goal range, the goal indicator not being displayed on the display screen if the current value is determined to not be within the goal range.

2. The system of claim 1, wherein the physiological parameter is at least one of intracranial pressure (ICP), cerebral perfusion pressure (CPP), mean arterial blood pressure (MAP), oxygen saturation ($pO_2$), heart rate, and temperature.

3. The system of claim 1, wherein causing the goal indicator to be displayed on the screen facilitates a decision of a medical practitioner whether the patient currently needs at least one of medical assessment and treatment.

4. The system of claim 1, wherein the processor is configured to receive the plurality of values of a physiological parameter from one or more sensors configured to gather physiological data.

5. A method, comprising:
receiving a plurality of values of a physiological parameter measured from a patient over a period of time;
determining if a current value based on the received values is within a normal range of the physiological parameter;
causing an alarm indicator to be displayed on a display screen if the current value is determined to not be within the normal range, the alarm indicator not being displayed on the display screen if the current value is determined to be within the normal range;
determining if the current value is within a goal range of the physiological parameter, the goal range being a subset of the normal range; and
causing a goal indicator to be displayed on the display screen if the current value is determined to be within the goal, the goal indicator not being displayed on the display screen if the current value is determined to not be within the goal range.

6. The method of claim 5, wherein causing the goal indicator to be displayed on the display screen comprises changing a color shown in a first portion of the display screen, and causing the alarm indicator to be displayed on the display screen comprises changing a color shown in a second portion of the display screen.

7. The method of claim 5, further comprising determining if a plurality of the values match a predetermined pattern, the goal indicator not being displayed on the display screen if the plurality of values are determined to match the predetermined pattern even if the current value is determined to be within the goal range.

8. The method of claim 7, wherein the predetermined pattern comprises at least one of the plurality of values continuously increasing toward an upper limit of the normal range and the plurality of values continuously decreasing toward a lower limit of the normal range.

9. The method of claim 7, wherein a number of the plurality of values is a predetermined number.

10. The method of claim 5, wherein the display screen is attached to a housing, and wherein the determining if the current value is within the normal range, the causing the alarm indicator to be displayed, the determining if the current value is within the goal range, and the causing the goal indicator to be displayed are performed by a processor disposed in the housing.

11. The method of claim 5, wherein the display screen is attached to a housing, and wherein the determining if the current value is within the normal range, the causing the alarm indicator to be displayed, the determining if the current value is within the goal range, and the causing the goal indicator to be displayed are performed by a processor remotely located from the housing.

12. The method of claim 5, wherein the physiological parameter is at least one of intracranial pressure (ICP), cerebral perfusion pressure (CPP), mean arterial blood pressure (MAP), oxygen saturation ($pO_2$), heart rate, and temperature.

13. A method, comprising:
receiving data representing a value of a physiological parameter over a time period, the physiological parameter being measured from a patient;
displaying, on a monitoring screen, a current value based on the received values;
determining if the current value is within a goal range of the physiological parameter, the goal range having a predetermined upper limit and a predetermined lower limit;
determining if the current value is within a normal range of the physiological parameter, the normal range having a predetermined upper limit that is greater than the predetermined upper limit of the goal range and having a predetermined lower limit that is less than the predetermined lower limit of the goal range, wherein one of determining if the current value is within the goal range and determining if the current value is within the normal range occurs after the other;
if the current value is determined to be within the goal range, causing a visual goal indicator indicating that the current value is within the goal range to be displayed on the monitoring screen, the goal indicator not being displayed on the monitoring screen if the current value is determined to not be within the goal range; and
if the current value is determined to be outside the normal range, causing a visual alarm indicator indicating that the current value is outside the normal range to be displayed on the monitoring screen, the alarm indicator not being displayed on the monitoring screen if the current value is determined to be within the normal range.

14. The method of claim 13, wherein causing the visual goal indicator to be displayed on the monitoring screen comprises changing a color shown in a first portion of the monitoring screen adjacent the current value, and causing the visual alarm indicator to be displayed on the monitoring screen comprises changing a color shown in a second portion of the monitoring screen adjacent the current value.

15. The method of claim 13, wherein the goal indicator is not displayed on the monitoring screen if the alarm indicator is displayed on the monitoring screen, and the alarm indicator is not displayed on the monitoring screen if the goal indicator is displayed on the monitoring screen.

16. The method of claim 13, further comprising:
continuously repeating the determining if the current value is within the goal range so as to continuously update on the monitoring screen whether or not the goal indicator is displayed on the monitoring screen; and
continuously repeating the determining if the current value is within the normal range so as to continuously update on the monitoring screen whether or not the alarm indicator is displayed on the monitoring screen.

17. The method of claim 13, further comprising:
receiving data representing a value of a second physiological parameter over the time period, the second physiological parameter being measured from the patient; and
changing at least one of the predetermined upper limit of the goal range and the predetermined lower limit of the goal range based on an current value of the value of the second physiological parameter over the time period.

18. The method of claim 13, further comprising:
receiving data representing a value of one or more additional physiological parameters over time, each of the one or more additional physiological parameters being measured from the patient;
displaying, on the monitoring screen, a graphical representation of an current value of each of the one or more additional physiological parameters over the time period;
determining if the current value of each of the one or more additional physiological parameters is within a respective goal range for each of the one or more additional physiological parameters, each of the respective goal ranges having a predetermined upper limit and a predetermined lower limit;
if the current value of any of the one or more additional physiological parameters is determined to be within its associated goal range, causing a visual goal indicator indicating that the current value is within the goal range to be displayed on the monitoring screen, the goal indicator for the one or more additional physiological parameters not being displayed on the monitoring screen if its associated current value is determined to be outside its associated goal range;
determining if the current value of each of the one or more additional physiological parameters is within a respective normal range for each of the one or more additional physiological parameters, each of the respective normal ranges having a predetermined upper limit that is greater than the predetermined upper limit of its associated goal range and having a predetermined lower limit that is less than the predetermined lower limit of its goal range; and
if the current value of any of the one or more additional physiological parameters is determined to be outside its associated normal range, causing a visual alarm indicator indicating that the current value is outside the normal range to be displayed on the monitoring screen, the alarm indicator for the one or more additional physiological parameters not being displayed on the monitoring screen if its associated current value is determined to be within its associated normal range.

19. The method of claim 13, further comprising setting the predetermined upper limit of the goal range and the predetermined lower limit of the goal range in response to a manual user input indicating the predetermined upper limit of the goal range and the predetermined lower limit of the goal range.

20. The method of claim 13, further comprising preprogramming the predetermined upper limit of the goal range and the predetermined lower limit of the goal range based on a typical normal range of the physiological parameter.

21. The method of claim 13, wherein the physiological parameter is at least one of intracranial pressure (ICP), cerebral perfusion pressure (CPP), mean arterial blood pressure (MAP), oxygen saturation ($pO_2$), heart rate, and temperature.

22. The method of claim 13, wherein causing the visual alarm indicator to be displayed on the monitoring screen indicates to medical personnel monitoring the monitoring screen that the patient's condition is not stable.

* * * * *